US008236907B2

(12) United States Patent
Marks et al.

(10) Patent No.: US 8,236,907 B2
(45) Date of Patent: Aug. 7, 2012

(54) NEUTRAL BIMETALLIC TRANSITION METAL PHENOXYIMINATO CATALYSTS AND RELATED POLYMERIZATION METHODS

(75) Inventors: Tobin J. Marks, Evanston, IL (US); Brandon A. Rodriguez, Evanston, IL (US); Massimiliano Delferro, Chicago, IL (US)

(73) Assignee: Northwestern University, Evanston, IL (US)

( * ) Notice: Subject to any disclaimer, the term of this patent is extended or adjusted under 35 U.S.C. 154(b) by 484 days.

(21) Appl. No.: 12/574,397

(22) Filed: Oct. 6, 2009

(65) Prior Publication Data

US 2010/0121008 A1     May 13, 2010

Related U.S. Application Data

(60) Provisional application No. 61/105,116, filed on Oct. 14, 2008.

(51) Int. Cl.
 *C08F 4/80* (2006.01)
 *C08F 4/70* (2006.01)
 *C07F 15/04* (2006.01)
 *B01J 23/755* (2006.01)

(52) U.S. Cl. ........ 526/117; 526/118; 526/172; 526/348; 526/352; 526/281; 526/329.7; 556/146; 556/141; 556/136; 502/100

(58) Field of Classification Search .................. 526/117, 526/118
See application file for complete search history.

(56) References Cited

U.S. PATENT DOCUMENTS 7,435,701 B2 * 10/2008 Shen et al. .................... 502/113
2006/0270811 A1    11/2006 Shen et al.

OTHER PUBLICATIONS

Salata, M. R. and Marks, T. J., J. Am. Chem. Soc., 2008, 130, 12-13.*
Connor EF, Younkin TR, Henderson JI, Waltman AW, Grubbs RH. Synthesis of neutral nickel catalysts for ethylene polymerization—the influence of ligand size on catalyst stability. Chem. Commun., 2003, pp. 2272-2273.
Ittel SD, Johnson LK. Late-Metal Catalysts for Ethylene Homo- and Copolymerization. Chem. Rev. 2000, 100, pp. 1169-1203.
Gibson VC, Spitzmesser, SK. Advances in Non-Metallocene Olefin Polymerization Catalysts. Chem. Rev. 2003, 103, pp. 283-315.
Connor EF, Younkin TR, Henderson JI, Hwang S, Grubbs RH; Roberts WP; Litzau JJ. Linear Functionalized Polyethylene Prepared with Highly Active Neutral Ni(II) Complexes. J. Polym. Sci. Part A.: Polym. Chem. 40: pp. 2842-2854, 2002.
Salata MR, Marks TJ. Synthesis, Characterization, and Marked Polymerization Selectivity Characteristics of Binuclear Phenoxyiminato Organozirconium Catalysts. J. Am. Chem. Soc., 2008, 130, pp. 12-13.
Rodriguez BA; Delferro M, Marks TJ. Bimetallic Effects for Enhanced Polar Comonomer Enchainment Selectivity in Catalytic Ehtylene Polymerization. J. Am. Chem. Soc., 2009, 131, pp. 5902-5919.
Wang C, Friedrich S, Younkin TR, Li RT, Grubbs RH; Bansleben DA, Day MW. Neutral Nickel(II)-Based Catalysts for Ethylene Polymerization. Organometallics 1998, 17, pp. 3149-3151.

(Continued)

*Primary Examiner* — Rip A. Lee
(74) *Attorney, Agent, or Firm* — Reinhart Boerner Van Deuren s.c.

(57) ABSTRACT

A catalyst composition comprising a neutral bimetallic diphenoxydiiminate complex of group 10 metals or Ni, Pd or Pt is disclosed. The compositions can be used for the preparation of homo- and co-polymers of olefinic monomer compounds.

14 Claims, 22 Drawing Sheets

OTHER PUBLICATIONS

Li H; Marks TJ. Nuclearity and cooperativity effects in binuclear catalysts and cocatalysts for olefin polymerization. PNAS, Oct. 17, 2006, vol. 103, No. 42, pp. 15295-15302.

Younkin TR, Connor EF, Henderson JI, Friedrich SK, Grubbs RH, Bansleben. Neutral, Single-Component Nickel (II) Polyolefin Catalysts That Tolerate Heteroatoms. Science, vol. 287, Jan. 21, 2000, pp. 460-462. www.sciencemag.org.

* cited by examiner

FI-Ni-A, L = PMe₃, R = Me
FI-Ni-B, L = PPh₃, R = Napth

FI²-Ni₂-A, P = PMe₃

FI²-Ni₂-B, P' = PPh₃

NEUTRAL BIMETALLIC TRANSITION METAL PHENOXYIMINATO CATALYSTS AND RELATED POLYMERIZATION METHODS

This application claims priority benefit from application Ser. No. 61/105,116 filed Oct. 14, 2008, incorporated herein by reference in its entirety.

This invention was made with government support under Grant No. CHE 04157407 awarded by the National Science Foundation and Grant No. DE-FG02-86ER13511 awarded by the Department of Energy. The government has certain rights in the invention.

BACKGROUND OF THE INVENTION

The remarkable enchainment cooperativity effects displayed by single-site group 4 bimetallic olefin polymerization catalysts include significantly enhanced activity, chain branching, and comonomer enchainment selectivity. Moreover, these effects scale approximately inversely with the intermetallic distance, and are evident in both constrained geometry and aryloxyiminato group 4 catalysts, as depicted below for $Ti_2$ and $FI^2$—$Zr_2$, respectively.

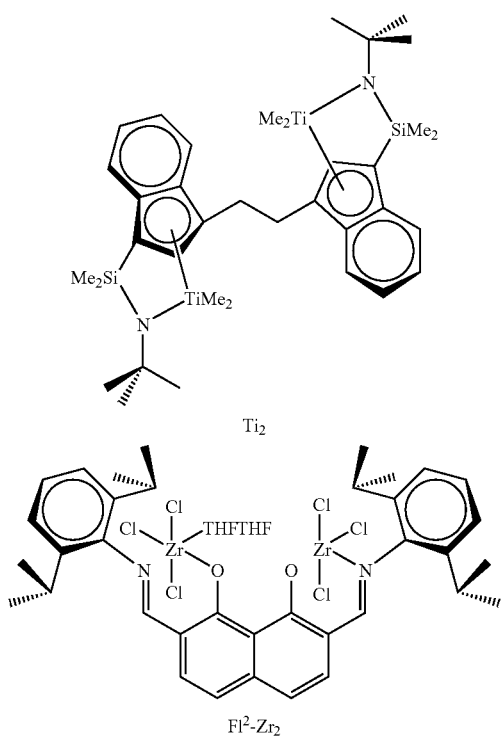

However studies to date have focused exclusively on group 4 metals. There remains an on-going effort in the art to extend such catalysts to include other metal centers to better realize the benefits and advantages available from such systems.

SUMMARY OF THE INVENTION

In part, this invention can be directed to a catalyst composition comprising a neutral bimetallic diphenoxydiiminate complex of a formula

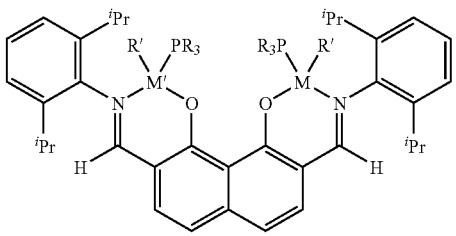

where M and M' can be independently selected from group 10 metal atoms or centers selected from Ni, Pd and Pt; each R can be a moiety independently selected from alkyl and aryl moieties; and each R' can be a moiety independently selected from alkyl and aryl moieties. While the imino phenyl substituents are shown as isopropyl, each such substituent can, alternatively, be selected from various other alkyl and/or aryl moieties. Such substitution is limited only by steric or other functional effect consistent with polymerization reactions of the sort described herein. Without limitation, in such embodiments, M and M' can both be Ni. In certain such embodiments, each of R and each of R' can be independently selected from methyl and naphthyl moieties.

In part, the present invention can also be directed to a method of preparing an addition polymer. Such a method can comprise combining a catalyst composition of the sort described herein and one or more ethylenically unsaturated monomeric compounds; and polymerizing the monomeric compound(s) in the presence of such a catalyst composition, to form an addition polymer. As would be understood by those skilled in the art, an ethylenically unsaturated monomeric compound can refer to a molecule comprising one or more carbon-carbon double bonds, capable of an insertion addition polymerization.

Regardless, such a method can be used in conjunction with one or more polar olefinic monomeric compounds, one or more non-polar olefinic monomeric compounds and/or combinations of such polar and non-polar compounds. Such compounds are limited only by polymerization upon combination or contact with a catalytic composition of the sort described herein. Accordingly, such a method can be used to prepare an addition polymer selected from poly(polar olefin)s, poly (non-polar olefin)s, poly[(polar olefin)-(nonpolar olefin)]s and combinations thereof. With regard to the latter, any such copolymer can be a random, alternating, or block copolymer. In certain embodiments, ethylene can be used for either homo- or co-polymerization. In certain other non-limiting embodiments, whether in the context of homo- or co-polymerization, a polar olefinic monomeric compound can comprise an acrylate moiety. Such a monomeric compound can be selected from various methacrylate compounds, including but not limited to methyl methacrylate.

Without limitation, a catalyst composition used in conjunction with such a method can comprise a metal atom/center pair at an internuclear distance at least partially sufficient to provide a degree of cooperativity during polymerization. As would be understood by those skilled in the art made aware of this invention, cooperativity in the context of a bimetallic catalyst system can refer to the influence of one metal atom/center on the other metal atom/center to polymerize an ethylenically unsaturated monomeric compound. Without limitation as to any one theory, mechanism or mode of operation, cooperativity can comprise one metal atom/center modifying the electronic, steric or another spatial environment of the other metal atom/center, affecting the insertion of such a monomeric compound, and/or the growth of a polymeric chain from or otherwise associated with the other metal/atom center.

Accordingly, the present invention can also be directed toward a method of using a bimetallic catalyst composition of this invention for (1) homopolymerization of an ethylenically unsaturated monomeric compound; and (2) to affect and/or enhance co-monomeric enchainment; and (3) in conjunction with either (1) or (2), to increase methyl group chain branching. With regard to co-polymerization, in certain embodiments, such a method can be used for the incorporation of one or more polar olefinic monomeric compounds into a co-polymer, such affect and/or enhancement as compared to results achieved by mononuclear analogs of the prior art. Regardless, such a method of using a bimetallic catalyst composition can be absent the presence of a co-catalyst compound of the prior art.

DETAILED DESCRIPTION OF CERTAIN EMBODIMENTS

Figure 1A:
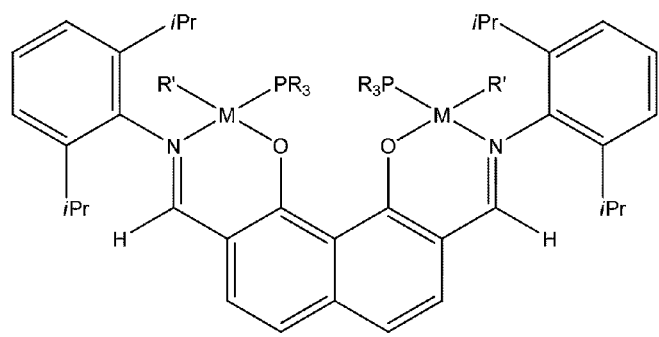
FIG. 1A depicts the bimetallic diphenoxydiiminate of the invention.
Figure 1B:
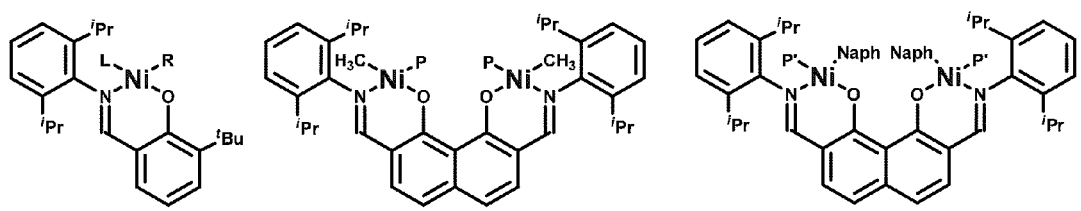
FIG. 1B depicts specific binuclear napthldioxydiiminato Ni(II) catalysts.

Various embodiments of this invention can be exemplified by bimetallic diphenoxydiiminates (FIG. 1A). This general ligand architecture confers distinctive electronic, steric, and catalytic characteristics on the metal center. For instance, binuclear napthldioxydiiminato Ni(II) catalysts such as FI$^2$—Ni$_2$-A and FI$^2$—Ni$_2$—B provide a rigid ligation which enforces effective Ni . . . Ni distances (e.g., as small as ~3.1 Å), and promotes cooperative polymerization and copolymerization effects (FIG. 1B). Such catalysts exhibit significant cooperativity effects—the first reported for a group 10 metal—manifested in enhanced polymerization activity, enhanced methyl chain branching, and enhanced comonomer incorporation under mild reaction conditions, and do not require a cocatalyst.

With reference to examples 1-6, the sodium salt of ligand FI$^2$—H$_2$2$^2$ was obtained by treating 2,7-di(2,6-diisopropylphenyl)imino-1,8-dihydroxy-naphthalene with NaH in THF, and bimetallic catalysts FI$^2$—Ni$_2$-A and FI$^2$—Ni$_2$—B were prepared as shown in Scheme 1. The imine protons in the Ni$_2$FI$^2$-A $^1$H NMR spectrum exhibit a characteristic $J_{PH}$~9 Hz, corresponding to PMe$_3$ coordination trans to the ketimine (confirmed by $^1$H NOESY). Close proximity of the Ni—CH$_3$ group and the methyls of one $^i$Pr group is also detected. In contrast, $J_{PH}$~6 Hz and the $^1$H NOESY indicate cis PPh$_3$ binding in FI$^2$—Ni$_2$—B. The $^{31}$P singlets in both complexes are consistent with the proposed FI$^2$—Ni$_2$-A and FI$^2$—Ni$_2$—B symmetries. In a similar manner, as would be understood by those skilled in the art, various other bimetallic catalyst compositions can be prepared with the corresponding metal (e.g., Pt, Pd, etc.) phosphine reagent.

For control experiments, mononuclear FI—Ni-A and FI—Ni—B were synthesized by reaction of the corresponding mono-salicylaldiminate sodium salt with the aforementioned Ni(II) precursors. In both monometallic complexes, the PR$_3$ (R=Me, Ph) ligand is bound trans to the ketimine group ($J_{PH}$~9 Hz). A second monometallic control complex was prepared by reaction of 1.0 equiv. of the Ni(II) precursor with the disodium salt of FI$^2$—H$_2$, followed by addition of TMSCl in situ to yield FI$^2$(TMS)-Ni (Scheme 1). Stepwise Ni incorporation can be monitored by integration of the now inequivalent i-propyl and imine $^1$H NMR resonances. These monometallic complexes are designed to probe the nature and extent of Ni—Ni cooperativity effects on polymerization.

Figure 2:
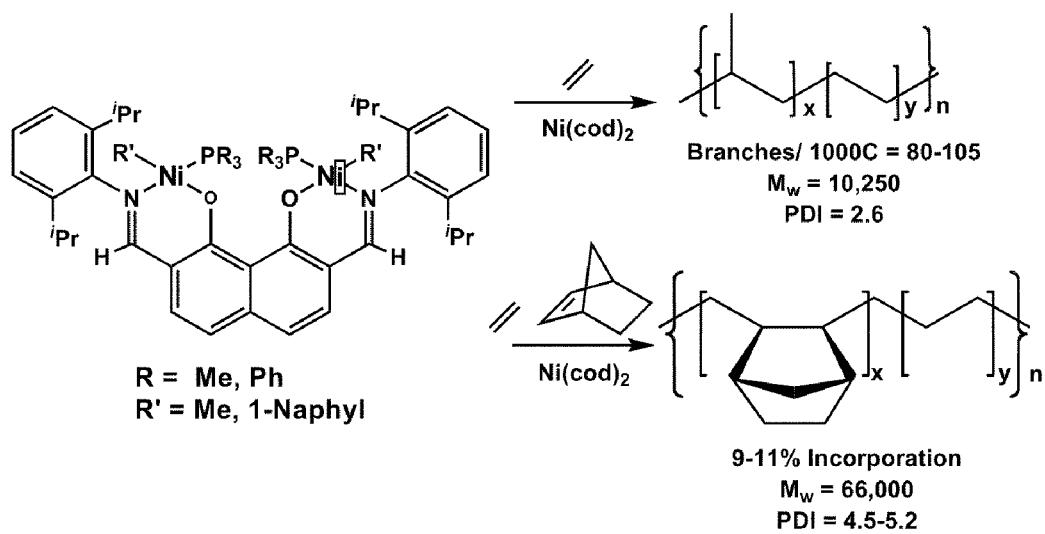
FIG. 2 is a scheme of the ethylene homopolymerization reactions carried out using the catalysts of the invention.

Room temperature ethylene homopolymerizations using the present catalysts were carried out in the presence of the phosphine scavenger/cocatalyst Ni(cod)$_2$ under conditions minimizing mass transport and exotherm effects (FIG. 2). Bimetallic FI$^2$—Ni$_2$-A and FI$^2$—Ni$_2$—B afford polyethylenes with molecular weights comparable to those produced by the mononuclear analogues and with polydispersities consistent with single-site processes (Table 1). However, the bimetallic catalysts exhibit a two-fold greater polymerization activity along with increased methyl (and only methyl-see below) branching. The branch density by $^1$H NMR8 is ~2× that achieved by the mononuclear catalysts under identical reaction conditions, and is confirmed by depressed DSC-determined melting points (Table 1). In the absence of a cocatalyst, the mononuclear systems do not produce polyethylene. In contrast, the present bimetallic catalysts produce polyethylenes with increased branching densities and concurrently depressed melting points, albeit at somewhat reduced polymerization rates versus the cocatalyzed polymerizations (Table 1). This particular productivity difference between FI$^2$—Ni$_2$-A, FI$^2$—Ni$_2$—B and the mononuclear analogues may reflect phosphine dissociation-related steric and electronic factors. Typically, equilibria between such phosphine-coordinated and uncoordinated species heavily favor the former, however the proximate bulky phosphine ligands in FI$^2$—Ni$_2$-A and FI$^2$—Ni$_2$—B may favor phosphine dissociation.

Scheme 1. Synthesis of Binuclear Catalysts FI$^2$-Ni$_2$-A and FI$^2$—Ni$_2$—B, and Mononuclear Catalyst FI$^2$TMS—Ni.

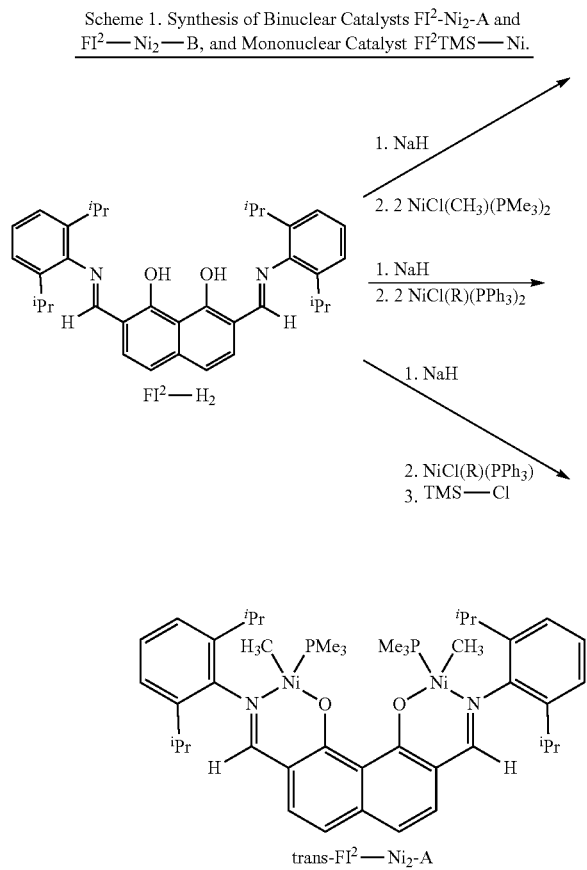

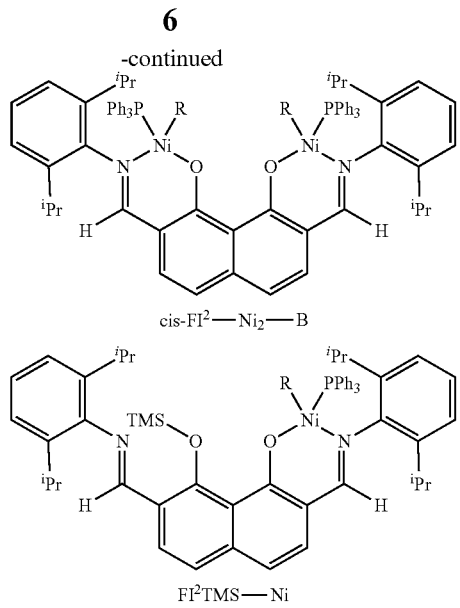

R = 1-Naphthyl

Control homopolymerization experiments were also carried out with catalyst FI$^2$TMS-Ni having a single Ni center bound to the FI$^2$ ligand. The results (Table 1) indicate comparable polymerization activities and branch densities than mononuclear catalysts FI—Ni-A and FI—Ni—B under identical conditions, and argue that the FI$^2$ ligand alone does not ensure enhanced homopolymerization activity or branching. While most data in Table 1 are the result of 40 minutes polymerization trials, ethylene polymerizations were also carried out for 60 and 90 minutes, with four of the catalysts, and the results verify continuing polymerization activity beyond 40 minutes. Homopolymerizations at higher temperatures ($\geq$40° C.), with or without cocatalyst, yield minimal polymer. Rather, bis-chelating Ni$_2$ (FI$^2$)$_2$L$_2$ complexes are identified, reminiscent of the analogous mononuclear phenoxyiminato catalysts.

Figure 3:
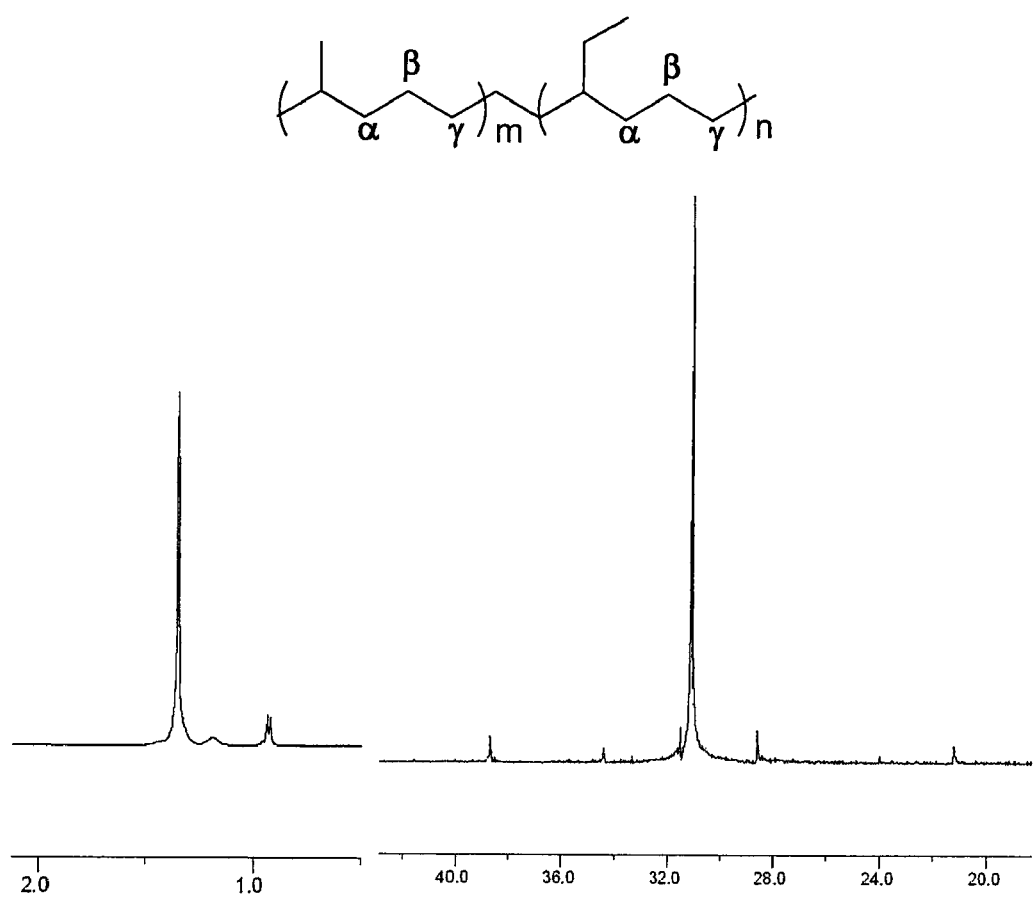
FIG. 3 depicts $^1$H and $^{13}$C NMR spectra of polyethylenes obtained from the monometallic catalysts at 130° C. at 400 MHz in tetrachloroethane.
Figure 4:
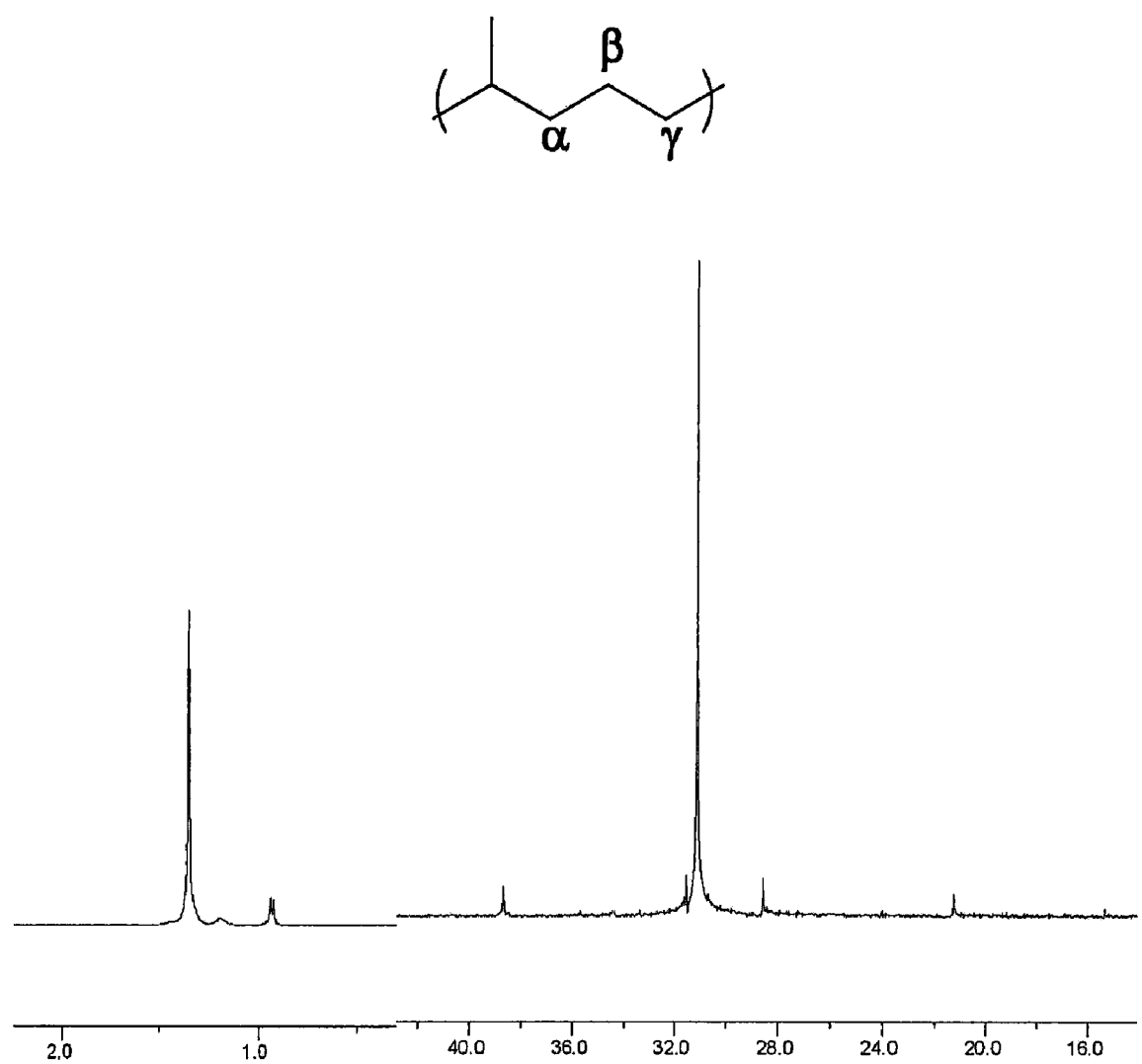
FIG. 4 shows $^1$H and $^{13}$C NMR spectra of polyethylenes obtained from the bimetallic catalysts at 130° C. at 400 MHz in tetrachloroethane.
Figure 5:
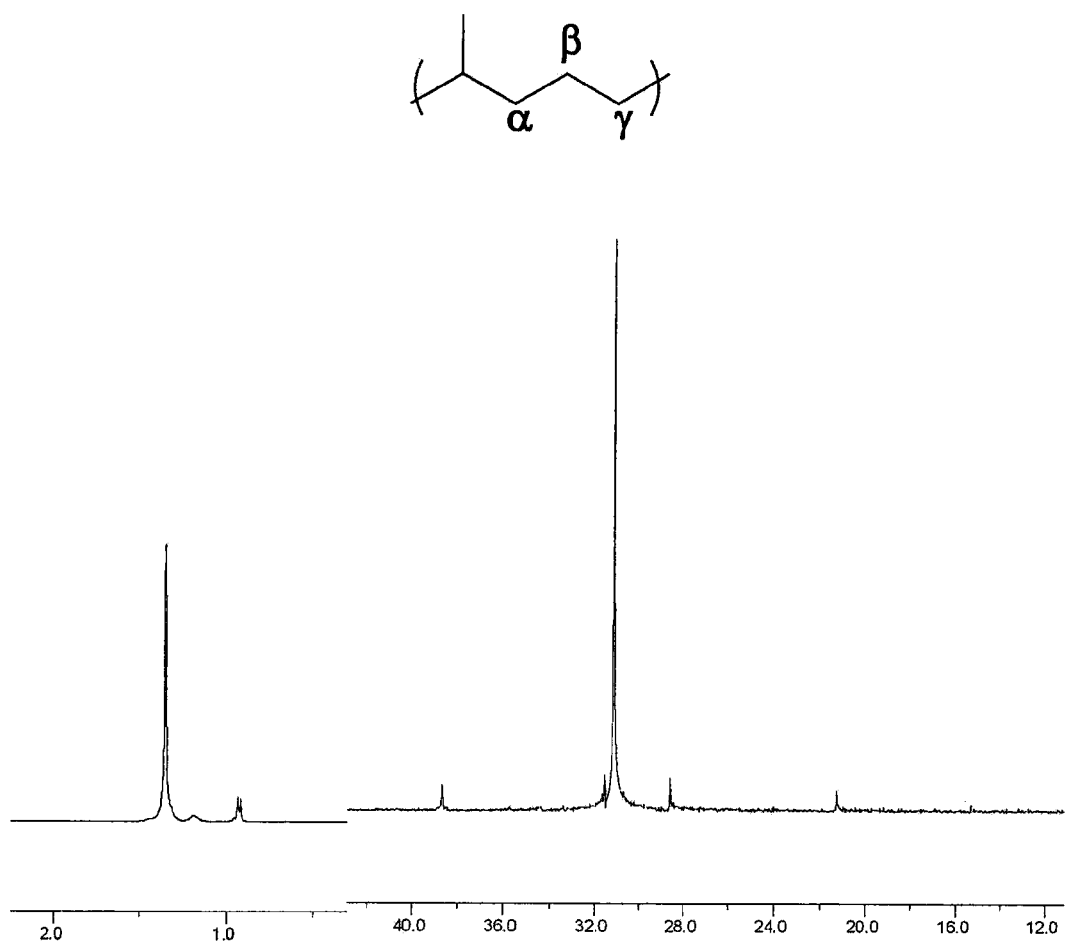
FIG. 5 depicts $^1$H and $^{13}$C NMR spectra of polyethylenes obtained from the bimetallic catalysts without using a cocatalyst at 130° C. at 400 MHz in tetrachloroethane.

In regard to homopolymer microstructure, the $^{13}$C NMR spectra of the polyethylenes produced by all of the monometallic catalysts exhibit five prominent non-polyethylene backbone resonances assignable to methyl branches, ethyl branches, and carbons α, β, and γ to the branches at δ 21.0, 35.0, 39.1, 28.2, and 31.5 ppm, respectively. (FIG. 3) In contrast, note that the polyethylenes derived from the bimetallic catalysts contain almost exclusively methyl branches. Thus, the $^{13}$C NMR spectra of the FI$^2$—Ni$_2$-A/FI$^2$—Ni$_2$—B derived products exhibit, in addition to backbone resonances, only four prominent signals, assignable to methyl branches and carbons α, β, and γ to the branch at δ 21.0, 39.1, 28.2, and 31.5 ppm, respectively. (FIGS. 4-5) The extent of ethyl branching amounts to $\leq$1% of the total branching. While further mechanistic experiments will be required to define additional aspects of the branch-forming pathways, at this stage it appears likely that the presence of the second Ni center suppresses insertion pathway 2 versus pathway 1 (Scheme 2) via an interplay of Ni$_2$ associated steric and electronic/coordination factors.

Scheme 2. Branch Formation Pathways in FI²—Ni₂-Mediated Ethylene Homopolymerization.

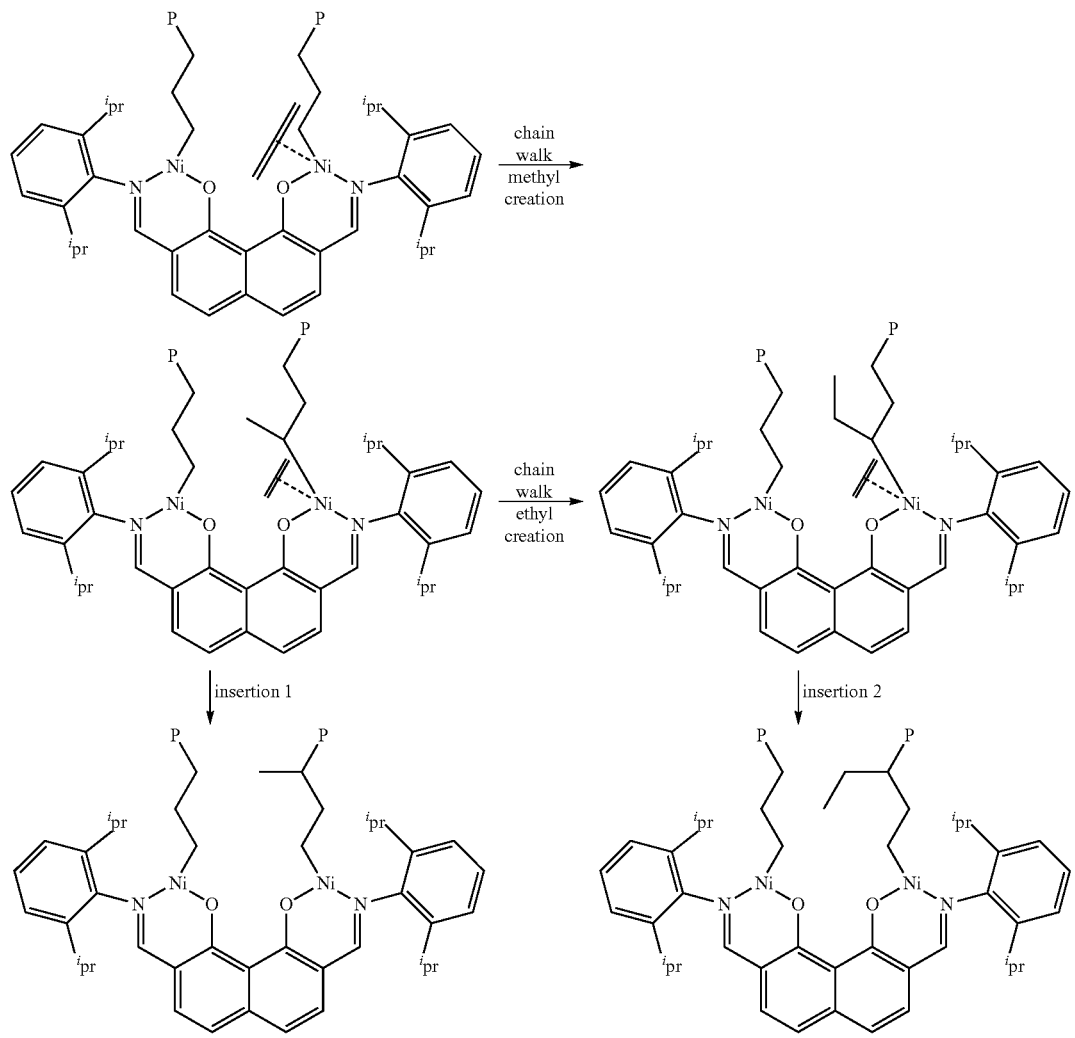

Figure 6:
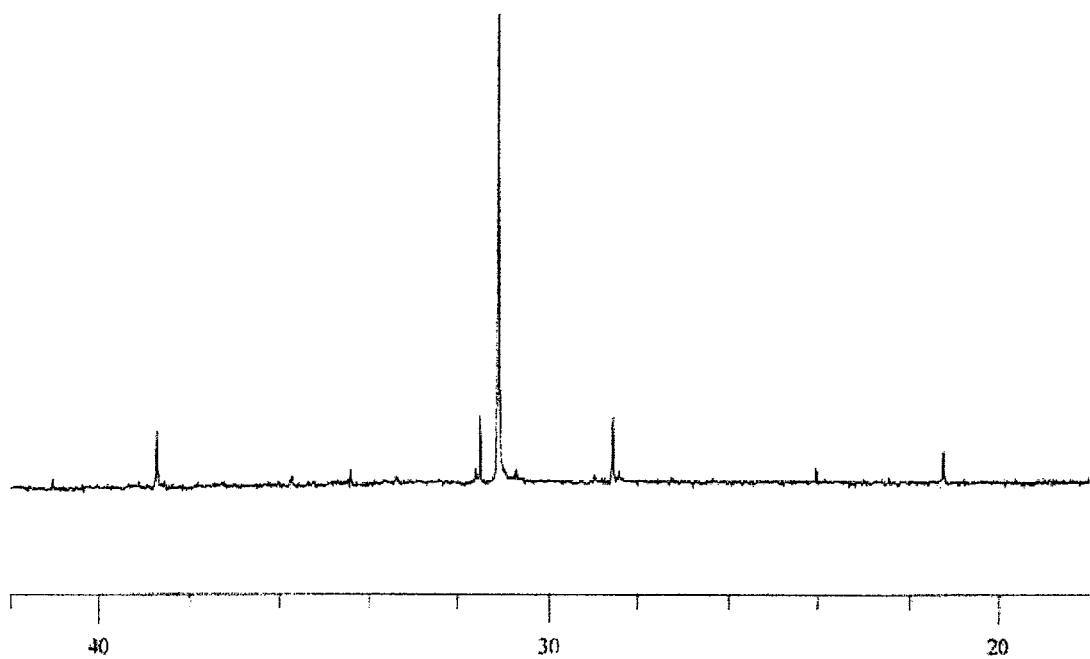
FIG. 6 is a $^{13}$C NMR spectrum of poly(co-norbornene) ethylenes obtained from the monometallic catalysts at 130° C. at 400 MHz in tetrachloroethane.

Ethylene+norbornene copolymerizations were also investigated (FIG. 2). Modest comonomer enchainment levels were achieved with the present mononuclear catalysts, in accord with results for comparable mononuclear systems. (FIG. 6 and Table 1). In FIG. 6, the smaller signals at δ 41.0, 35.8, and 33.0 ppm correspond to co-enchained norbornene.

Figure 7:
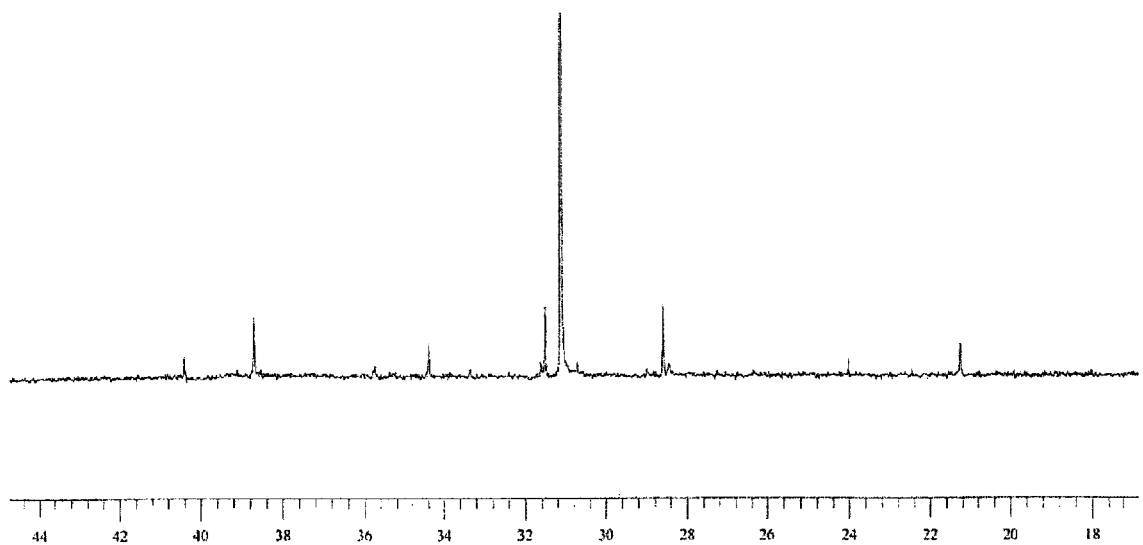
FIG. 7 is a $^{13}$C NMR spectrum of poly(co-norbornene) ethylenes obtained from the bimetallic catalysts at 130° C. at 400 Mhz in tetrachloroethane.

In marked contrast, ethylene+norbornene copolymerizations mediated by binuclear FI²—Ni₂-A and FI²—Ni₂—B proceed with 3-4× greater activity and achieved 3-4× greater selectivity for comonomer enchainment, while product molecular weights are comparable (as in the homopolymerization cases) (FIG. 7).

TABLE 1

Ethylene and Ethylene-co-Norbornene Polymerization Data for Nickel FI²-Ni₂, FI²-Ni, and FI Catalysts.

| Entry | Catalyst | Cocatalyst | Comonomer | Polymer Yield (g) | $M_w{}^d$ | $M_w/M_n$ | Total Me/ 1000 C.[e] | m.p °C.[f] | Activ.[g] | Comon. Incorp.[h] |
|---|---|---|---|---|---|---|---|---|---|---|
| 1 | FI²-Ni₂-A[a] | Ni(cod)₂ | — | 0.663 | 10300 | 2.6 | 80 | 68 | 7.1 | — |
| 2 | FI²-Ni₂-B[a] | Ni(cod)₂ | — | 0.684 | 10100 | 2.6 | 93 | 66 | 7.4 | — |
| 3 | FI²-Ni₂-B[j] | Ni(cod)₂ | — | 0.631 | 10700 | 2.6 | 92 | 68 | 6.8 | — |
| 4 | FI²-Ni₂-B[k] | Ni(cod)₂ | — | 0.566 | 10900 | 2.6 | 86 | 68 | 6.2 | — |
| 5 | FI-Ni-A[a] | Ni(cod)₂ | — | 0.167 | 11700 | 2.5 | 52 | 93 | 3.6 | — |
| 6 | FI-Ni-B[a] | Ni(cod)₂ | — | 0.175 | 10500 | 2.5 | 54 | 97 | 3.7 | — |
| 7 | FI²TMS-Ni[a] | Ni(cod)₂ | — | 0.141 | 11200 | 2.6 | 40 | 98 | 3.3 | — |
| 8 | FI²-Ni₂-A[b] | — | — | 0.103 | 6000 | 2.7 | 102 | 60 | 0.2 | — |
| 9 | FI2-Ni₂-B[b] | — | — | 0.196 | 7000 | 2.7 | 105 | 61 | 0.4 | — |
| 10 | FI-Ni-A[b] | — | — | i | — | — | — | — | — | — |
| 11 | FI-Ni-B[b] | — | — | i | — | — | — | — | — | — |

TABLE 1-continued

Ethylene and Ethylene-co-Norbornene Polymerization Data for Nickel FI$^2$-Ni$_2$, FI$^2$-Ni, and FI Catalysts.

| Entry | Catalyst | Cocatalyst | Comonomer | Polymer Yield (g) | M$_w$[d] | M$_w$/M$_n$ | Total Me/1000 C.[e] | m.p ° C.[f] | Activ.[g] | Comon. Incorp.[h] |
|---|---|---|---|---|---|---|---|---|---|---|
| 12 | FI$^2$-Ni$_2$-A[c] | Ni(cod)$_2$ | Norbornene | 0.558 | 66400 | 5.2 | 34 | 107 | 1.3 | 9 |
| 13 | FI$^2$-Ni$_2$-B[c] | Ni(cod)$_2$ | Norbornene | 0.504 | 65800 | 4.5 | 38 | 106 | 1.2 | 11 |
| 14 | FI-Ni-A[c] | Ni(cod)$_2$ | Norbornene | 0.072 | 63200 | 2.3 | 9 | 124 | 0.3 | 3 |
| 15 | FI-Ni-B[c] | Ni(cod)$_2$ | Norbornene | 0.066 | 64000 | 2.1 | 11 | 124 | 0.3 | 3 |

[a]Polymerizations carried out with 10 μmol catalyst and 2 equiv cocatalyst/Ni at 25° C. for 40 min in 25 mL of toluene at 7.0 atm ethylene.
[b]Polymerizations carried out with 20 μmol of catalyst at 25° C. for 2 h in 25 mL toluene at 7.0 atm ethylene.
[c]Polymerizations carried out with 20 μmol catalyst and 2 equiv cocatalyst/Ni at 25° C. for 90 min in 25 mL toluene and 225 equiv norbornene at 7.0 atm ethylene.
[d]GPC vs polyethylene standard; uncorrected.
[e]By $^1$H NMR.
[f]Determined by DSC.
[g]Kg polyethylene/mol of Ni · h atm.
[h]Molar percentage by 13C NMR.
i No polymer obtained.
[j]Polymerizations carried out with 10 μmol catalyst and 2 equiv cocatalyst/Ni at 25° C. for 60 min in 25 mL of toluene at 7.0 atm ethylene.
[k]Polymerizations carried out with 10 μmol catalyst and 2 equiv cocatalyst/Ni at 25° C. for 90 min in 25 mL of toluene at 7.0 atm ethylene.

These results show that, for single-site d$^8$ Ni(II) aryloxy-iminato ethylene polymerization catalysts, a proximate catalytically-active Ni site substantially increases activity, degree of and selectivity for, methyl group branching, and comonomer incorporation selectivity versus the mononuclear analogues. Furthermore, these binuclear catalysts produce highly branched polyethylenes in the absence of a cocatalyst.

While the preceding discussion illustrates group 10 binuclear effects for non-polar olefins, this invention is also shown to substantially increase selectivity for polar-functionalized (e.g., norbornene and methyl methacrylate) co-enchainment, as compared to analogous mononuclear controls, and enhance activity in polar solvents. To that effect, bimetallic catalysts FI$^2$—Ni$_2$-A and FI$^2$—Ni$_2$—B, as well as mononuclear control catalysts FI—Ni-A, FI—Ni—B, and FI$^2$-TMS-Ni were synthesized and purified as provided in examples 7-11. These controls are designed to provide a single Ni site in either an analogous FI ligand or in the same FI$^2$ ligand but with one Ni site occupied by an inert, sterically similar TMS group. Polymerizations were carried out under rigorously anaerobic conditions, with appropriate attention to mass transport and exotherm effects, as appropriate, and with Ni(cod)$_2$ as the cocatalyst. Polymers were characterized by $^1$H/$^{13}$C NMR, DSC, and GPC (Table 2). Ethylene homopolymerizations were carried out in toluene, then with added polar reagents, and activities decline in the order, toluene>diethyl ether>acetone>water. While polar additives reduce polymerization activity, in each case the binuclear catalyst is ~3× more active than the mononuclear analogue (Table 2) and achieves far greater branching (~6× for entry 3 vs. 4). Attempts to conduct polymerizations at higher temperatures result in minimal polymer yield and formation of coordinatively saturated L$_2$Ni$_2$ species, characterized by single-crystal X-ray diffraction (not shown).

Figure 8:
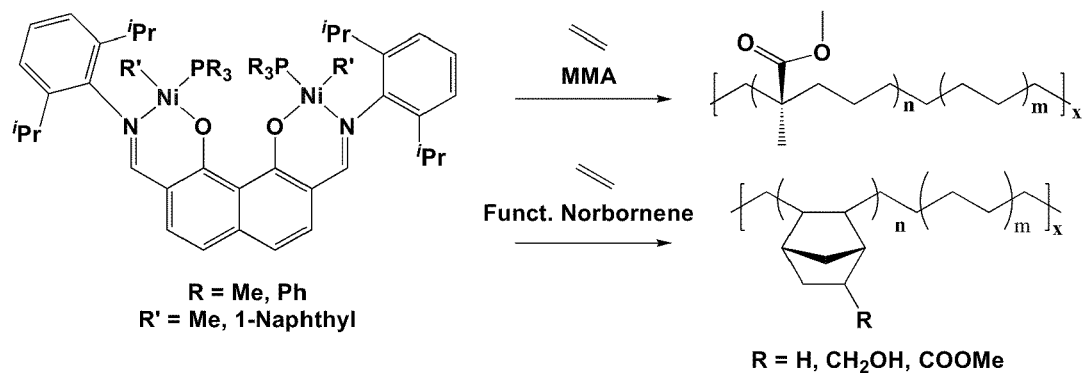
FIG. 8 is a scheme of FI$^2$/FI/FI$^2$-TMS-catalyzed copolymerizations of ethylene with polar-functionalized NBs and MMA.

FI$^2$/FI/FI$^2$-TMS-catalyzed copolymerizations of ethylene with polar-functionalized norbornenes (NBs), methyl acrylate (MA), and methyl methacrylate (MMA) were carried out under reaction conditions typically used for similar monometallic FI catalysts and afford copolymers with relatively low polar comonomer incorporation levels (see FIG. 8 and Table 2). In marked contrast, the FI$^2$—Ni$_2$ catalysts exhibit 3-4× enhancements in polar comonomer enchainment selectivity versus the monometallic controls, regardless of the polar substituent. Minimal influence of NB substituents is observed. While the present and related mononuclear Ni catalysts incorporate minimal MA and MMA in ethylene copolymerizations under the present conditions, FI$^2$—Ni$_2$-A and FI$^2$—Ni$_2$—B enchain significant quantities (7-8 mol % with MMA, 8-9% in the case of MA) while simultaneously maintaining high methyl branch densities. (PE methyl branching densities were determined by $^1$H NMR spectroscopy using the ratio of methyl group to the overall number of carbon (methyl+methylene+methine) integrals.) Essentially monomodal GPC traces as well as DSC and $^{13}$C NMR spectroscopic data confirm that these are homogeneous, random copolymers and not simple heterogeneous mixtures of polyethylene and acrylate homopolymer—demonstrating the first non-MAO activated neutrally-charged Ni catalysts capable of incorporating substantial quantities of MA and MMA into polyethylenes.

TABLE 2

Ethylene Polymerizations in the Presence of Polar Solvent Additives and Polar Comonomers

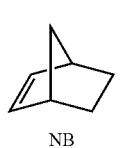 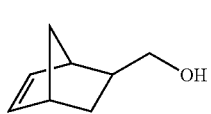 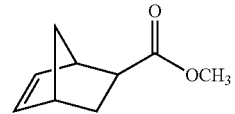 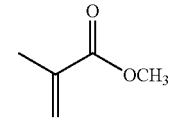

NB     NB1     NB2     MMA

| Entry | Catalyst | Additive/ Comonomer | Polymer Yield (g) | M$_w$[c] | M$_w$/M$_n$ | Branches/ 1000 C[d] | m.p ° C.[e] | Activity[f] | Comonomer Incorporation[g] |
|---|---|---|---|---|---|---|---|---|---|
| 1 | FI$^2$-Ni$_2$B | — | 0.684 | 10060 | 2.6 | 93 | 66 | 7.4 | — |
| 2 | FI-Ni-B | — | 0.175 | 10500 | 2.5 | 54 | 97 | 3.7 | — |

TABLE 2-continued

Ethylene Polymerizations in the Presence of Polar Solvent Additives and Polar Comononers

NB    NB1    NB2    MMA

| Entry | Catalyst | Additive/ Comonomer | Polymer Yield (g) | $M_w{}^c$ | $M_w/M_n$ | Branches/ 1000 C[d] | m.p ° C.[e] | Activity[f] | Comonomer Incorporation[g] |
|---|---|---|---|---|---|---|---|---|---|
| 3 | FI²-Ni₂-B[a] | Ethyl Ether | 0.314 | 13220 | 5.2 | 81 | 72 | 2.3 | — |
| 4 | FI-Ni-B[a] | Ethyl Ether | 0.060 | 12010 | 2.4 | 13 | 98 | 0.9 | — |
| 5 | FI²-Ni₂-B[a] | Acetone | 0.074 | 21100 | 5.8 | 90 | 78 | 0.5 | — |
| 6 | FI-Ni-Ba | Acetone | 0.009 | 19090 | 2.9 | [i] | 103 | 0.1 | — |
| 7 | FI²-Ni₂B[a] | Water | 0.036 | 23690 | 3.9 | 39 | 122 | 0.3 | — |
| 8 | FI-Ni-B[a] | Water | 0.006 | 21805 | 3.1 | [i] | 122 | 0.1 | — |
| 9 | FI²-Ni₂-A[b] | NB1 | 0.488 | 62600 | 4.6 | 39 | 101 | 1.2 | 8 |
| 10 | FI²-Ni₂-B[b] | NB1 | 0.502 | 63490 | 4.8 | 33 | 105 | 1.2 | 9 |
| 11 | FI²TMS-Ni[b] | NB1 | 0.054 | 62900 | 2.0 | 12 | 122 | 0.3 | ≦1 |
| 12 | FI-Ni-A[b] | NB1 | 0.067 | 64940 | 2.0 | 9 | 122 | 0.3 | ≦2 |
| 13 | FI-Ni-B[b] | NB1 | 0.059 | 63850 | 2.1 | 9 | 122 | 0.3 | 3 |
| 14 | FI²-Ni₂-A[b] | NB2 | 0.467 | 62840 | 5.0 | 37 | 112 | 1.1 | 8 |
| 15 | FI²-Ni₂-B[b] | NB2 | 0.454 | 64830 | 4.6 | 39 | 110 | 1.1 | 8 |
| 16 | FI-Ni-A[b] | NB2 | 0.043 | 62130 | 2.3 | 8 | 128 | 0.2 | ≦2 |
| 17 | FI-Ni-B[b] | NB2 | 0.052 | 65490 | 2.6 | 9 | 126 | 0.2 | 2 |
| 18 | FI²-Ni₂B[b] | MMA | 0.700 | 7970 | 1.4 | 48 | 106 | 1.7 | 8 |
| 19 | FI-Ni-B[b] | MMA | [h] | — | — | — | — | — | — |
| 20 | FI2TMS-Ni[b] | MMA | [h] | — | — | — | — | — | — |

[a]Polymerizations carried out with 10 μmol catalyst and 2 equiv cocatalyst/Ni center at 25° C. + 1500 equiv. polar additive for 40 min in 25 mL toluene at 7.0 atm ethylene pressure.
[b]Polymerizations carried out with 10 μmol catalyst and 2 equiv. cocatalyst/Ni center at 25° C. + 225 equiv. of polar additive for 60 min in 25 mL toluene at 7.0 atm ethylene pressure.
[c]By GPC vs polyethylene standards, uncorrected.
[d]By ¹H NMR.
[e]Melting temperature by DSC.
[f]Kg polyethylene/(mol of Ni · h · atm).
[g]Molar percentage determined by ¹³C NMR.
[h]Negligible polymer obtained.
[i]Insufficient sample for analysis.

These results show that the introduction of two catalytically-active group 10 centers in close, rigidly-held proximity can achieve significantly enhanced polar comonomer incorporation and chain branching in neutrally-charged phenoxyiminato Ni(II) ethylene polymerization catalysts. These results suggest the agency of species such as I in the enchainment process. (Scheme 3) Without limitation to any one theory, mechanism or mode of operation, the origin of these effects most likely involves secondary binding to weakly basic monomer functional groups (e.g., I where B is a polar functional group or in other systems can be C—H or an arene π-system), which modifies relative chain transfer and enchainment rates.

FI—Ni-A, L = PMe₃, R = Me
FI—Ni—B, L = PPh₃, R = 1-Napthyl

-continued

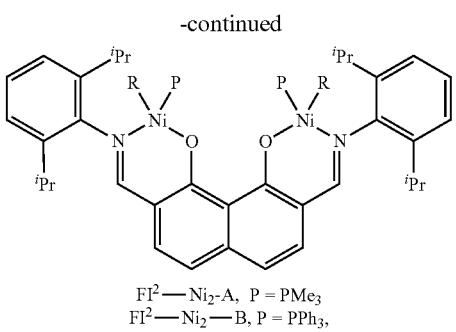

FI²—Ni₂-A, P = PMe₃
FI²—Ni₂—B, P = PPh₃,

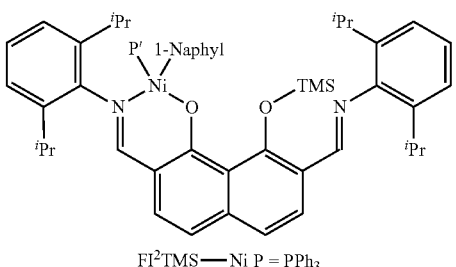

FI²TMS—Ni P = PPh₃

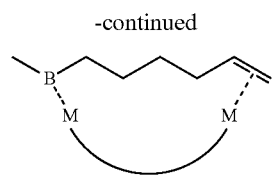

I

EXAMPLES OF INVENTION

The following non-limiting examples and data illustrate various aspects and features relating to the compounds, compositions and/or methods of the present invention, including the preparation of catalyst compositions comprising bimetallic metal atom/centers and use thereof in polymerization reactions of the sort described herein. In comparison with the prior art, the present methods, compounds and compositions provide results and data which are surprising, unexpected and contrary thereto. While the utility of this invention is illustrated through the use of several catalyst compositions and bimetallic metal atom/centers, ligands and monomeric compounds which can be used therewith, it will be understood by those skilled in the art that comparable results are obtained with various other catalyst compositions, metal centers/ligands, and monomeric compounds to provide a range of homo- and co-polymers, as are commensurate with the scope of this invention.

Materials and Methods. All manipulations of air-sensitive materials were performed with rigorous exclusion of oxygen and moisture in flamed Schlenk-type glassware on a dual manifold Schlenk line, or interfaced to a high-vacuum line ($10^{-5}$ Torr), or in a nitrogen-filled Vacuum Atmospheres glove box with a high capacity recirculator (<1 ppm $O_2$). Argon and ethylene (Matheson, polymerization grade) were purified by passage through a supported MnO oxygen-removal column and an activated Davison 4A molecular sieve column. Ether solvents were purified by distillation from Na/K alloy/benzophenone ketyl. Hydrocarbon solvents (n-pentane and toluene) were dried using activated alumina columns according to the method described by Grubbs, and were additionally vacuum-transferred from Na/K alloy immediately before vacuum line manipulations. All solvents for high-vacuum line manipulations were stored in vacuo over Na/K alloy in Teflon-valve sealed bulbs. Deuterated solvents were obtained from Cambridge Isotope Laboratories (all≧99 atom % D), were freeze pump-thaw degassed, dried over Na/K alloy and were stored in resealable flasks. Other non-halogenated solvents were dried over Na/K alloy, and halogenated solvents were distilled from $CaH_2$ and stored over activated Davison 4A molecular sieves. The reagents trans-[NiMeCl(PMe_3)_2], trans-[Ni(Naph)Cl(PPh_3)_2] (Naph=1-naphthyl), 2,7-di(2,6-diisopropylphenyl)imino-1,8-dihydroxynaphthalene, salicylaldimine and salicylaldiminate sodium salt were prepared according to literature procedures. [Ni(cod)_2] (cod=1,5-cyclooctadiene) was purchased from Aldrich.

Physical and Analytical Measurements. NMR spectra were recorded on Varian$^{UNITY}$(Inova-500 (FT, 500 MHz, $^1$H; 125 MHz, $^{13}$C, $^{UNITY}$Inova-400 (FT, 400 MHz, $^1$H; 100 MHz, $^{13}$C) and Mercury-400 (FT 400 MHz, $^1$H; 100 MHz, $^{13}$C; 162 MHz, $^{31}$P). Chemical shifts (δ) for $^1$H and $^{13}$C spectra were referenced using internal solvent resonances and are reported relative to tetramethylsilane. Chemical shifts (δ) for $^{31}$P spectra were reported relative to an external 85% $H_3PO_4$ standard. NMR experiments on air-sensitive samples were conducted in Teflon valve-sealed sample tubes (J. Young). Elemental analyses were performed by Midwest Microlab, Indianapolis, Ind. $^{13}$C NMR assays of polymer microstructure were conducted in 1,1,2,2-tetrachloroethane-$d_2$ at 130° C. Signals were assigned according to the literature for polyethylene. Melting temperatures of polymers were measured by DSC (DSC 2920, TA Instruments, Inc.) from the second scan with a heating rate of 10° C./min. GPC measurements were performed on a Polymer Laboratories PL-GPC 220 instrument using 1,2,4-trichlorobenzene solvent (stabilized with 125 ppm BHT) at 150° C. A set of three PLgel 10 μm mixed columns was used. Samples were prepared at 160° C. Molecular weights were determined by GPC using narrow polystyrene standards and are not corrected.

The synthetic procedures detailed in examples 1-11 can be considered with reference to schemes 4-6, below.

Example 1

Synthesis of 2,7-Di-[(2,6-diisopropylphenyl)imino]-1,8-naphthalenediolate disodium salt (1). To a solution of 2,7-di (2,6-diisopropylphenyl)imino-1,8-dihydroxynapthalene (1.0 g, 1.87 mmol) in THF dry (30 mL) was added NaH (0.224, 9.35 mmol). The resulting mixture was stirred at room temperature for 1 hour, filtered, and the filtrate evaporated. The yellow residue was washed with pentane (30 mL) and dried in in vacuo. The resulting salt was immediately used without further purification in the following synthesis. Yield, 83%. $^1$H NMR (CDCl_3, 25° C., 500 MHz): δ=8.13 (s, 2H, HC=N), 7.53-6.75 (m, 10H, Ph) 3.07 (sept, 4H, $^3J_{HH}$=6.8 Hz, CHMe_2), 1.34 (s, 12H, CHMe_2).

Example 2

Synthesis of {2,7-Di-[(2,6-diisopropylphenyl)imino]-1,8-naphthalenediolato}bis[methyl)-(trimethylphosphine)Ni(II)] (2). A solution of 1 (0.900 g, 1.55 mmol) in $Et_2O$ (25 mL) was added dropwise at room temperature to a stirring solution of trans-[NiMeCl(PMe_3)_2] (0.815 g, 3.12 mmol) in benzene (25 mL) A rapid color change from yellow to dark red was observed, and after 1 hour the mixture became dark orange. After this time, the reaction mixture was filtered by cannula. The volatiles were then removed from the filtrate in vacuo and the residue was washed with pentane. A light orange powder of 2 was obtained. Yield, 73%. $^1$H NMR ($C_6D_6$, 25° C., 500 MHz): δ 7.65 (d, $^4J_{PH}$=8.0 Hz, 2H, HC=N), 7.13-6.43 (m, 10H, Ph), 4.13 (sept, 2H, $^3J_{HH}$=6.5 Hz, CHMe_2), 3.73 (sept, 2H, $^3J_{HH}$=6.5 Hz, CHMe_2), 1.56 (d, $^3J_{HH}$=6.5 Hz, 6H, CHMe_2), 1.31 (d, $^3J_{HH}$=6.5 Hz, 6H, CHMe_2), 1.15 (d, $^3J_{HH}$=6.5 Hz, 6H, CHMe_2), 1.08 (d, $^3J_{HH}$=6.5 Hz, 6H, CHMe_2), 1.06 (d, $^2J_{PH}$=9.5 Hz, 18H, PMe_3), −1.15 (d, $^3J_{PH}$=7.3 Hz, 6H, NiMe). $^{13}$C NMR ($C_6D_6$, 25° C., 125 MHz): δ 170.33, 163.93, 150.17, 145.26, 141.96, 133.50, 125.96, 123.91, 123.02, 115.97, 113.51, 28.47, 24.45, 14.15, −12.23. $^{31}$P NMR ($C_6D_6$, 25° C., 162 MHz): δ−7.58. Anal. Found: C, 63.12; H, 7.71; N, 3.29. Calcd. for $C_{44}H_{64}N_2Ni_2O_2P_2$: C, 63.49; H, 7.75; N, 3.37.

Example 3

Synthesis of {2,7-Di-[(2,6-diisopropylphenyl)imino]-1,8-naphthalenediolato}bis[(1-naphthyl)-(triphenylphosphine) Ni(II)] (3). A solution of 1 (0.800 g, 1.38 mmol) in $Et_2O$ (25 mL) was added dropwise at room temperature to a stirring solution of trans-[Ni(Naph)Cl(PPh_3)_2] (2.06 g, 2.76 mmol) in benzene (25 mL) A rapid color change from yellow to dark pink was observed, and after 2 hours the mixture became dark purple. After this time, the reaction mixture was filtered by cannula. The volatiles were next removed in vacuo from the filtrate and the residue was washed with pentane. A purple powder of 3 was obtained. Yield, 74%. $^1$H-NMR (C$_6$D$_6$, 25° C., 500 MHz): δ 11.07 (d, $^3J_{PH}$=14.0 Hz, 2H, Naph-H), 10.16 (d, $^4J_{PH}$=8.0 Hz, 2H, Naph-H), 8.90 (d, $^4J_{PH}$=8.0 Hz, 2H, Naph-H), 7.88 (d, $^4J_{PH}$=6.6 Hz, 2H, HC=N), 7.53-6.24 (m, 48H, Ph), 3.09 (sept, 2H, $^3J_{HH}$=6.9 Hz, CHMe$_2$), 1.22 (d, 3J$_{HH}$=6.9 Hz, 6H, CHMe$_2$). $^{13}$C NMR (C$_6$D$_6$, 25° C., 125 MHz): δ 177.47, 159.34, 152.28, 144.14, 140.62, 137.41, 134.14, 130.37, 129.91, 123.86, 122.50, 118.79, 113.20, 28.08, 22.96. $^{31}$P-NMR (C$_6$D$_6$, 25° C., 162 MHz): δ 33.2. Anal. Found: C, 77.16; H, 6.01; N, 2.11. Calcd. for C$_{92}$H$_{86}$N$_2$Ni$_2$O$_2$P$_2$: C, 77.33; H, 5.92; N, 1.96.

Example 4

Synthesis of {2,7-Di-[(2,6-diisopropylphenyl)imino]-1-naphthalenato}(1-naphthyl)-(triphenylphosphine)Ni(II). A solution of 1 (0.800 g, 1.38 mmol) in Et$_2$O (25 mL) was added dropwise at room temperature to a stirring solution of trans-[Ni(Naph)Cl(PPh$_3$)$_2$] (1.03 g, 1.38 mmol) in benzene (25 mL) A rapid color change from yellow to dark pink was observed, and after 2 hours the mixture became dark red. After this time, 1 equivalent of trimethylsilane-chloride was added to react with the second Na$^+$ site. The reaction mixture was then filtered by cannula. The volatiles were next removed from the filtrate in vacuo and the residue was washed with pentane. A red powder was obtained. Yield, 60%. $^1$H NMR (CDCl$_3$, 25° C., 500 MHz): δ=13.98 (s, 1H, OH), 8.13-8.22 (d, 2H, HC=N), 7.53-6.75 (m, 10H, Ph) 3.07 (m, 4H, $^3J_{HH}$=6.8 Hz, CHMe$_2$), 1.34 (s, 12H, CHMe$_2$). $^{31}$P-NMR (C$_6$D$_6$, 25° C., 162 MHz): δ 31.0. Anal. Found: C, 78.16; H, 6.19; N, 2.77. Calcd. for C$_{64}$H$_{63}$N$_2$NiO$_2$P: C, 78.29; H, 6.47; N, 2.85.

Example 5

Synthesis of {[2-(t-Butyl)-6-(2,6-diisopropylphenyl)imino]phenolato}(methyl)-(trimethylphosphine)Ni(II) (4). A solution of the salicylaldiminate sodium salt (0.400 g, 1.11 mmol) in Et$_2$O (30 mL) was added dropwise at room temperature to a solution of trans-NiMeCl(PMe$_3$)$_2$ (0.290 g, 1.11 mmol) in Et$_2$O (25 mL). The orange mixture was stirred for 2 hours at room temperature. After this time, the reaction mixture was filtered by cannula. The filtrate was then evaporated in vacuo and the solid residue was washed with pentane. A yellow-orange microcrystalline powder of 4 was obtained. Yield, 74%. $^1$H NMR (C$_6$D$_6$, 25° C., 500 MHz): δ 7.84 (d, $^4J_{PH}$=8.8 Hz, 1H, HC=N), 7.42-6.56 (m, 6H, Ph), 3.96 (sept, 1H, $^3J_{HH}$=6.7 Hz, CHMe$_2$), 1.51 (s, 9H, CMe$_3$), 1.32 (d, $^3J_{HH}$=6.7 Hz, 6H, CHMe$_2$), 0.97 (d, $^3J_{HH}$=6.7 Hz, 6H, CHMe$_2$), 0.95 (d, $^2J_{PH}$=9.1 Hz, 9H, PMe$_3$), −1.10 (d, $^3J_{PH}$=7 Hz, 3H, NiMe). $^{13}$C NMR (C$_6$D$_6$, 25° C., 125 MHz): δ 166.25, 149.49, 141.45, 140.62, 133.690, 126.220, 123.45, 120.19, 35.23, 29.80, 28.32, 22.45, 14.15, −17.32. $^{31}$P NMR (C$_6$D$_6$, 25° C., 162 MHz): δ−12.57. Anal. Found: C, 66.53; H, 8.63; N, 2.91. Calcd. for C$_{27}$H$_{42}$NNiOP: C, 66.69; H, 8.71; N, 2.88.

Example 6

Synthesis of {[2-(t-Butyl)-6-(2,6-diisopropylphenyl)imino]phenolato}(1-naphthyl)-(triphenylphosphine)Ni(II) (5). A solution of the salicylaldiminate sodium salt (0.500 g, 1.39 mmol) in benzene (30 mL) was added dropwise at room temperature to a stirring solution of trans-[Ni(Naph)Cl(PPh$_3$)$_2$] (1.037 g, 1.39 mmol) in benzene (25 mL) The orange mixture was stirred for 2 hours at room temperature. After this time, the reaction mixture was filtered by cannula filtration. The filtrate was then evaporated in vacuo and the solid residue was washed with ethanol. A yellow-orange microcrystalline powder of 5 was obtained. Yield, 75%. $^1$H NMR (C$_6$D$_6$, 25° C., 500 MHz): δ 10.47 (d, $^4J_{PH}$=8.8 Hz, 1H, NiC—CH$_{naph}$), 7.96 (d, $^4J_{PH}$=8.8 Hz 1H, HC=N), 7.69-6.55 (m, 24H, Ph), 5.56 (sept, 1H, $^3J_{HH}$=6.5 Hz, CHMe$_2$), 2.98 (sept, 1H, $^3J_{HH}$=6.5 Hz, CHMe$_2$), 1.68 (d, $^3J_{HH}$=6.6 Hz, 3H, CHMe$_2$), 1.10 (d, $^3J_{HH}$=6.6 Hz, 3H, CHMe$_2$), 0.90 (s, 9H, CMe$_3$), 0.85 (d, $^3J_{HH}$=6.6 Hz, 3H, CHMe$_2$), −0.07 (d, $^3J_{HH}$=6.6 Hz, 3H, CHMe$_2$). $^{13}$C NMR (C$_6$D$_6$, 25° C., 125 MHz): δ 167.11, 165.13, 150.59, 141.56, 140.51, 136.42, 134.82, 133.42, 132.16, 131.73, 129.55, 127.51, 125.79, 123.71, 122.18, 121.56, 120.70, 114.20, 34.67, 30.02, 28.45, 24.45, 21.43. $^{31}$P NMR (C$_6$D$_6$, 25° C., 162 MHz): δ 24.21. Anal. Found: C, 77.78; H, 6.81; N, 1.86. Calcd. for C$_{51}$H$_{52}$NNiOP: C, 78.07; H, 6.68; N, 1.79.

Example 7

Synthesis of 2,7-Di-[(2,6-diisopropylphenyl)imino]-1,8-naphthalenediolate disodium salt (1). To a solution of 2,7-di (2,6-diisopropylphenyl)imino-1,8-dihydroxynapthalene (1.0 g, 1.87 mmol) in THF dry (30 mL) was added NaH (0.224, 9.35 mmol). The resulting mixture was stirred at room temperature for 1 hour, filtered, and the filtrate evaporated. The yellow residue was washed with pentane (30 mL) and dried in in vacuo. This salt was immediately used without further purification in the following synthesis. Yield, 83%. $^1$H NMR (CDCl$_3$, 25° C., 500 MHz): δ=8.13 (s, 2H, HC=N), 7.53-6.75 (m, 10H, Ph) 3.07 (sept, 4H, $^3J_{HH}$=6.8 Hz, CHMe$_2$), 1.34 (s, 12H, CHMe$_2$).

Example 8

Synthesis of {2,7-Di-[(2,6-diisopropylphenyl)imino]-1-naphthalenato}(1-naphthyl)-(triphenylphosphine)Ni(II) sodium salt (2). A solution of 1 (0.800 g, 1.38 mmol) in Et$_2$O (25 mL) was added dropwise at room temperature to a stirring solution of trans-[Ni(Naph)Cl(PPh$_3$)$_2$] (1.03 g, 1.38 mmol) in benzene (25 mL) A rapid color change from yellow to dark pink was observed, and after 2 hours the mixture became dark red. The reaction mixture was then filtered by cannula. The volatiles were next removed from the filtrate in vacuo and the residue was washed with pentane. A red powder was obtained. Yield, 60%. $^1$H NMR (CDCl$_3$, 25° C., 500 MHz): δ=13.98 (s, 1H, OH), 8.13-8.22 (d, 2H, HC=N), 7.53-6.75 (m, 10H, Ph) 3.07 (m, 4H, $^3J_{HH}$=6.8 Hz, CHMe$_2$), 1.34 (s, 12H, CHMe$_2$). $^{31}$P-NMR (C$_6$D$_6$, 25° C., 162 MHz): δ 31.0. Anal. Found: C, 78.16; H, 6.19; N, 2.77. Calcd. for C$_{64}$H$_{63}$N$_2$NiO$_2$P: C, 78.29; H, 6.47; N, 2.85.

Example 9

Synthesis of {[2-(t-Butyl)-6-(2,6-diisopropylphenyl)imino]phenolato}(1-naphthyl)-(triphenylphosphine)Ni(II) trimethylsilane (3; FI$^2$TMS-Ni). To a solution of the 2 (0.500 g, 1.39 mmol) in benzene (30 mL) was added dropwise at room temperature to a stirring solution of TMS-Cl (1.39 mmol) in benzene (25 mL) The orange mixture was stirred for 2 hours at room temperature. After this time, the reaction mixture was filtered by cannula filtration. The filtrate was then evaporated in vacuo and the solid residue was washed with ethanol. A yellow-orange microcrystalline powder of 3 was obtained. Yield, 75%. $^1$H NMR (C$_6$D$_6$, 25° C., 500 MHz): δ 10.47 (d, $^4J_{PH}$=8.8 Hz, 1H, NiC—CH$_{naph}$), 7.96 (d, $^4J_{PH}$=8.8 Hz 1H, HC=N), 7.69-6.55 (m, 24H, Ph), 5.56 (sept, 1H, $^3J_{HH}$=6.5 Hz, CHMe$_2$), 2.98 (sept, 1H, $^3J_{HH}$=6.5 Hz, CHMe$_2$), 1.68 (d, $^3J_{HH}$=6.6 Hz, 3H, CHMe$_2$), 1.10 (d, $^3J_{HH}$=6.6 Hz, 3H, CHMe$_2$), 0.90 (s, 9H, CMe$_3$), 0.85 (d, $^3J_{HH}$=6.6 Hz, 3H, CHMe$_2$), −0.07 (d, $^3J_{HH}$=6.6 Hz, 3H, CHMe$_2$). $^{13}$C NMR (C$_6$D$_6$, 25° C., 125 MHz): δ 167.11, 165.13, 150.59, 141.56, 140.51, 136.42, 134.82, 133.42, 132.16, 131.73, 129.55, 127.51, 125.79, 123.71, 122.18, 121.56, 120.70, 114.20, 34.67, 30.02, 28.45, 24.45, 21.43. $^{31}$P NMR (C$_6$D$_6$, 25° C., 162 MHz): δ 24.21. Anal. Found: C, 77.78; H, 6.81; N, 1.86. Calcd. for C$_{51}$H$_{52}$NNiOP: C, 78.07; H, 6.68; N, 1.79.

Example 10

Synthesis of {[2-(t-Butyl)-6-(2,6-diisopropylphenyl) imino]phenolato}(methyl)(trimethyl-phosphine)Ni(II) (4; Fl$^2$Ni$_2$-A). A solution of the salicylaldiminate sodium salt (0.400 g, 1.11 mmol) in Et$_2$O (30 mL) was added dropwise at room temperature to a solution of trans-[NiMeCl(PMe$_3$)$_2$] (0.290 g, 1.11 mmol) in Et$_2$O (25 mL) The orange mixture was stirred for 2 hours at room temperature. After this time, the reaction mixture was filtered by cannula. The filtrate was then evaporated in vacuo and the solid residue was washed with pentane. A yellow-orange microcrystalline powder of 4 was obtained. Yield, 74%. $^1$H NMR (C$_6$D$_6$, 25° C., 500 MHz): δ 7.84 (d, $^4J_{PH}$=8.8 Hz, 1H, HC=N), 7.42-6.56 (m, 6H, Ph), 3.96 (sept, 1H, $^3J_{HH}$=6.7 Hz, CHMe$_2$), 1.51 (s, 9H, CMe$_3$), 1.32 (d, $^3J_{HH}$=6.7 Hz, 6H, CHMe$_2$), 0.97 (d, $^3J_{HH}$=6.7 Hz, 6H, CHMe$_2$), 0.95 (d, $^2J_{PH}$=9.1 Hz, 9H, PMe$_3$), −1.10 (d, $^3J_{PH}$=7 Hz, 3H, NiMe). $^{13}$C NMR (C$_6$D$_6$, 25° C., 125 MHz): δ 166.25, 149.49, 141.45, 140.62, 133.690, 126.220, 123.45, 120.19, 35.23, 29.80, 28.32, 22.45, 14.15, −17.32. $^{31}$P NMR (C$_6$D$_6$, 25° C., 162 MHz): δ −12.57. Anal. Found: C, 66.53; H, 8.63; N, 2.91. Calcd. for C$_{27}$H$_{42}$NNiOP: C, 66.69; H, 8.71; N, 2.88.

Example 11

Synthesis of {2,7-Di-[(2,6-diisopropylphenyl)imino]-1,8-naphthalenediolato}bis[(1-naphthyl)-(triphenylphosphine) Ni(II)] (5; Fl$^2$Ni$_2$—B). A solution of 1 (0.800 g, 1.38 mmol) in Et$_2$O (25 mL) was added dropwise at room temperature to a stirring solution of trans-[Ni(Naph)Cl(PPh$_3$)$_2$] (2.06 g, 2.76 mmol) in benzene (25 mL) A rapid color change from yellow to dark pink was observed, and after 2 hours the mixture became dark purple. After this time, the reaction mixture was filtered by cannula. The volatiles were next removed in vacuo from the filtrate and the residue was washed with pentane. A purple powder of 5 was obtained. Yield, 74%. $^1$H-NMR (C$_6$D$_6$, 25° C., 500 MHz): δ 11.07 (d, $^3J_{PH}$=14.0 Hz, 2H, Naph-H), 10.16 (d, $^4J_{PH}$=8.0 Hz, 2H, Naph-H), 8.90 (d, $^4J_{PH}$=8.0 Hz, 2H, Naph-H), 7.88 (d, $^4J_{PH}$=6.6 Hz, 2H, HC=N), 7.53-6.24 (m, 48H, Ph), 3.09 (sept, 2H, $^3J_{HH}$=6.9 Hz, CHMe$_2$, 1.22 (d, $^3J_{HH}$=6.9 Hz, 6H, CHMe$_2$). $^{13}$C NMR (C$_6$D$_6$, 25° C., 125 MHz): δ 177.47, 159.34, 152.28, 144.14, 140.62, 137.41, 134.14, 130.37, 129.91, 123.86, 122.50, 118.79, 113.20, 28.08, 22.96. $^{31}$P-NMR (C$_6$D$_6$, 25° C., 162 MHz): δ 33.2. Anal. Found: C, 77.16; H, 6.01; N, 2.11. Calcd. for C$_{92}$H$_{86}$N$_2$Ni$_2$O$_2$P$_2$: C, 77.33; H, 5.92; N, 1.96.

Scheme 4. Synthesis of ligand for bimetallic catalysts.

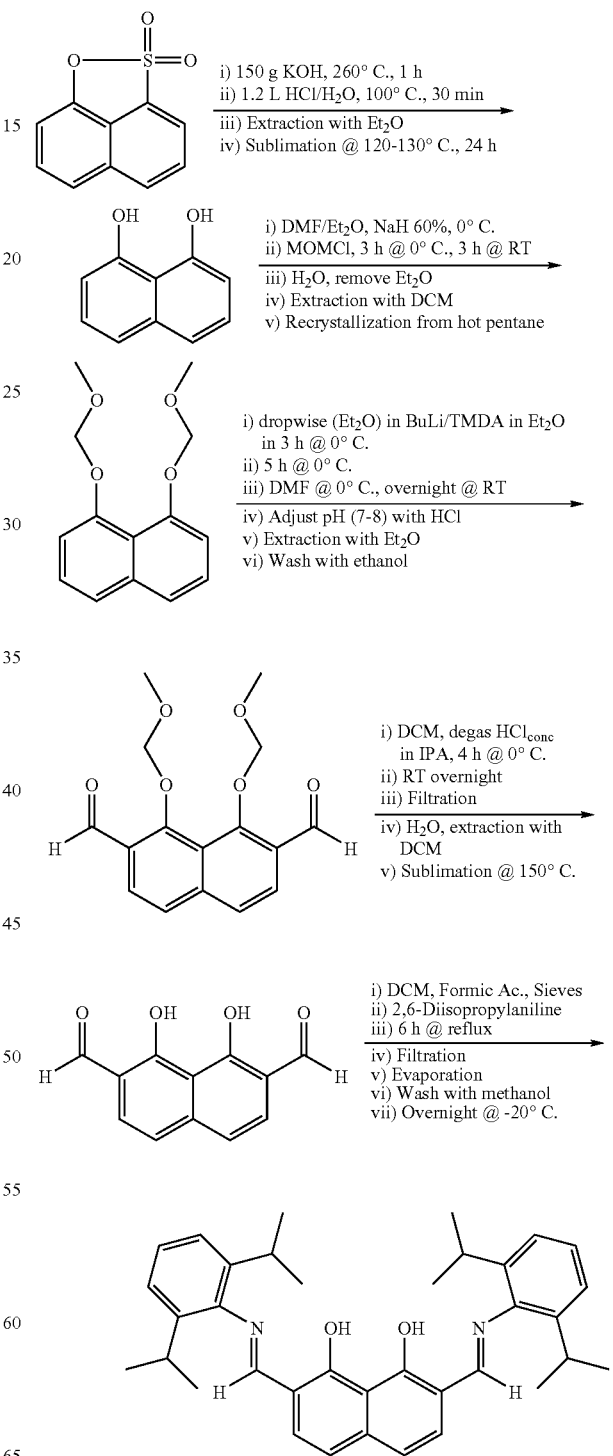

Scheme 5. Synthesis of ligand disodium salt.
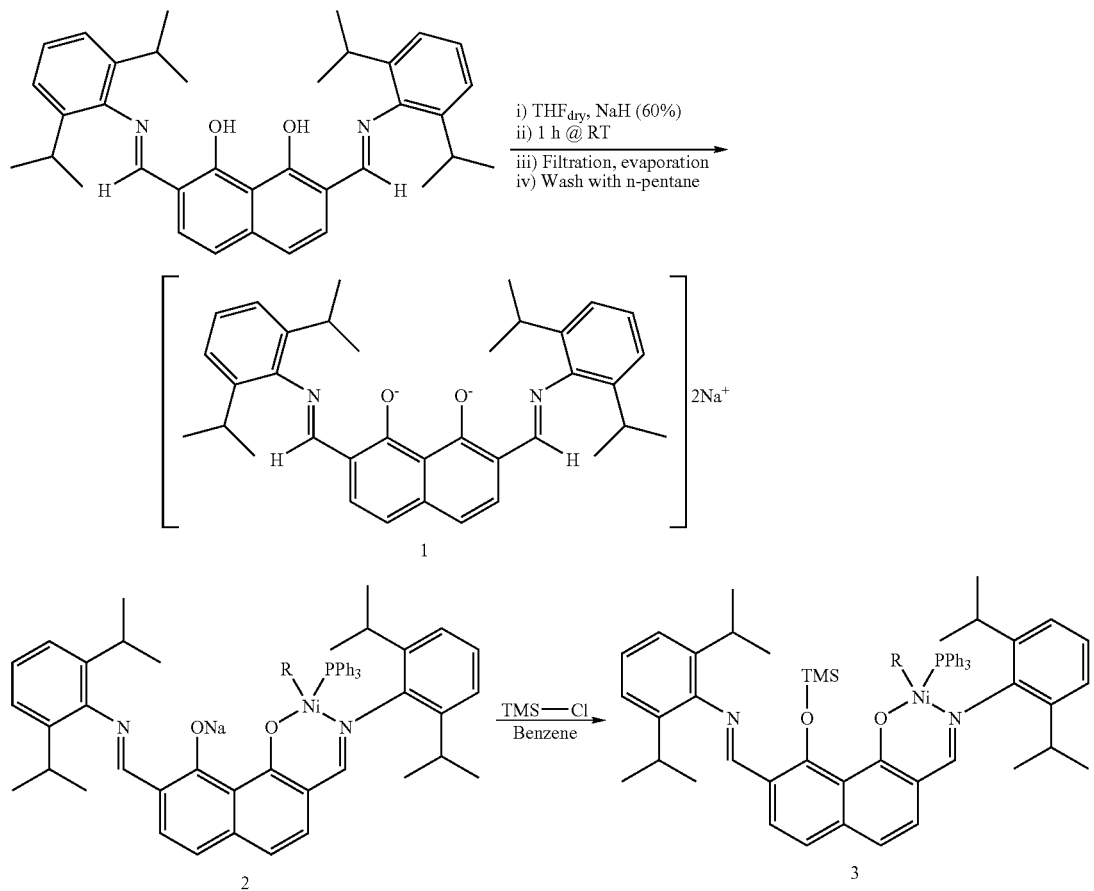
Scheme 6. Synthesis of Ni complexes 3, 4, and 5.
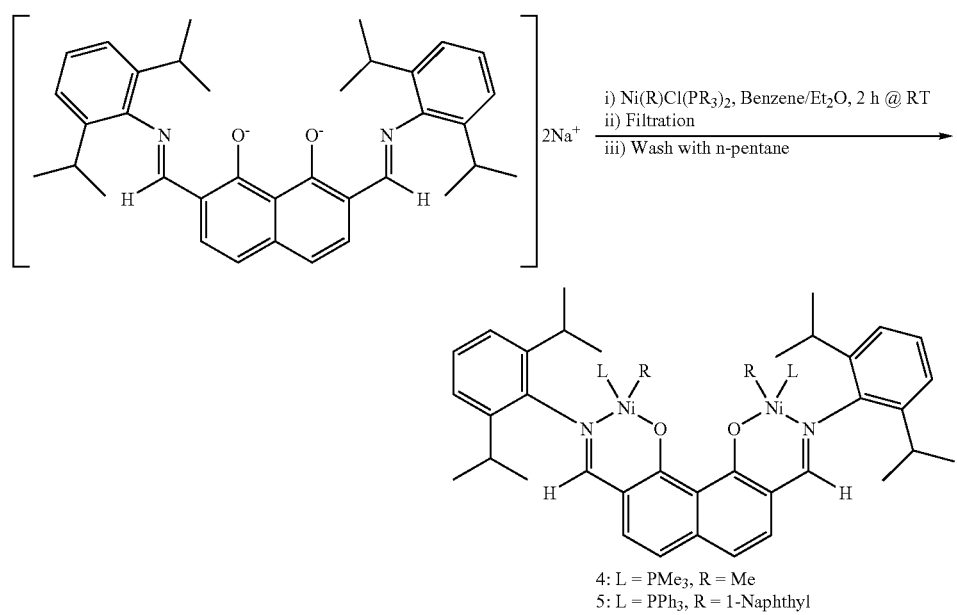
4: L = PMe₃, R = Me
5: L = PPh₃, R = 1-Naphthyl

Example 12

General Polymerization Procedure. A 200 mL glass pressure vessel was equipped with a large magnetic stirbar and was heated to the required temperature, with the temperature monitored by thermocouple. At no time was the temperature allowed to deviate more than 2° C. Next, 25 mL of toluene was injected into the reactor and the reactor was pressurized with ethylene to 1.0 atm. For single component trials, 20 μmol of catalyst solution was then injected and the pressure brought to 7.0 atm for 2 hours with rapid stirring. For cocatalyst-activated trials, a solution of 10 μmmol of catalyst in [Ni(cod)₂] was injected, after which the pressure was increased to 7.0 atm and rapid stirring maintained for 40 minutes. After the desired run time, the reactor was vented, and the reaction mixture was quenched with 10% HCl in ethanol. The precipitated polymer was stirred overnight, filtered, and dried under vacuum at 80° C. overnight.

Example 13

General procedure for Copolymerization of Ethylene and Norbornene by Ni complexes. A 200 mL glass pressure vessel was equipped with a large magnetic stirbar and heated to the required temperature. Next, 25 mL of toluene was injected into the reactor along with 225 eq. of norbornene. The reactor was then pressurized with ethylene to 1.0 atm. Next, 20 μmol of catalyst solution was injected and the pressure brought to 7.0 atm for 1.5 hours with rapid stirring. After the desired run time, the reactor was vented, and the reaction mixture was quenched with 10% HCl in ethanol. The precipitated polymer was stirred overnight, filtered, and dried under vacuum at 80° C. overnight.

Example 14

General Procedure for Ethylene Polymerizations. A dry, 200 mL glass pressure vessel was equipped with a large magnetic stirbar and heated to the required temperature. Next, 25 mL of toluene was injected into the reactor along with 1500 eq. of the desired rigorously degassed polar solvent additive. The reactor was then pressurized with ethylene to 1.0 atm. 10 μmol of catalyst solution was then injected and the pressure brought to 7.0 atm for 1 hour with rapid stirring. After the desired run time, the reactor was vented, and the reaction mixture was quenched with 10% HCl in ethanol. The precipitated polymer was stirred overnight, filtered, and dried under vacuum at 80° C. overnight.

Example 15

General Procedure for Ethylene Copolymerizations with MA, MMA, or Functionalized Norbornenes. A dry, 200 mL glass pressure vessel was equipped with a large magnetic stirbar and heated to the required temperature. Next, 25 mL of toluene was injected into the reactor along with 225 eq. of the desired polar comonomer. The reactor was then pressurized with ethylene to 1.0 atm. 20 μmol of catalyst solution was then injected and the pressure brought to 7.0 atm for 1.5 hours with rapid stirring. After the desired run time, the reactor was vented, and the reaction mixture was quenched with 10% HCl in ethanol. The precipitated polymer was stirred overnight, filtered, and dried under vacuum at 80° C. overnight.

Example 16

Figure 9:
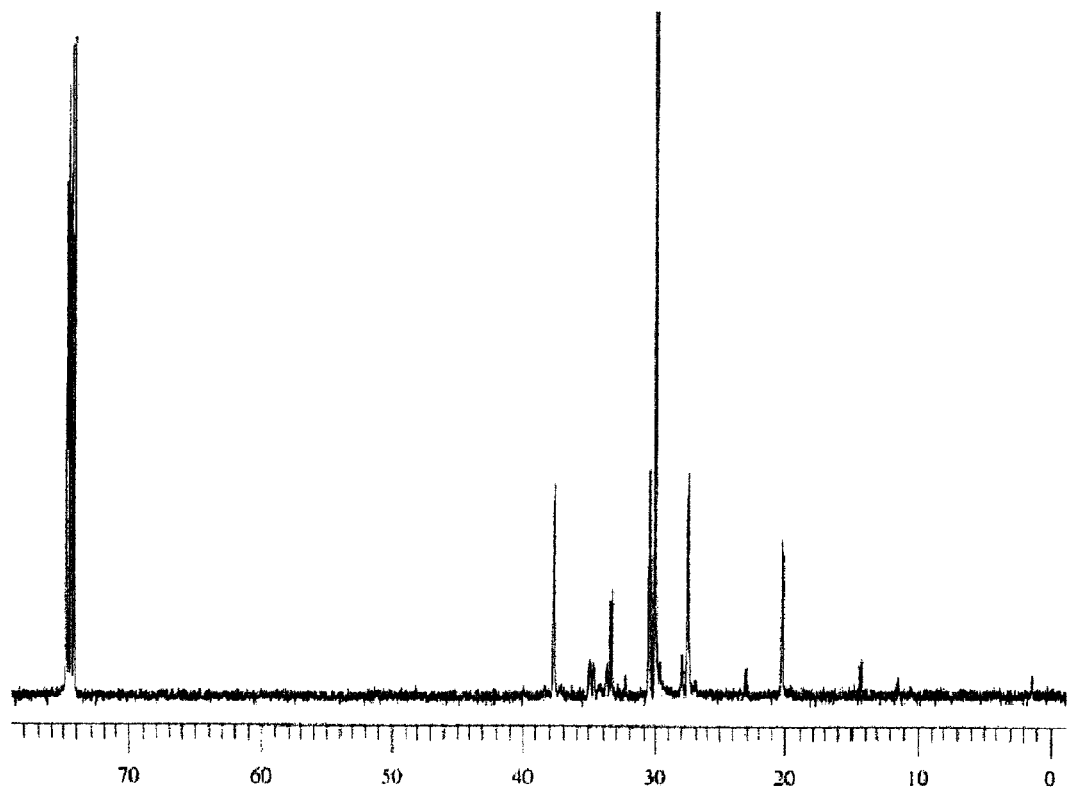
FIG. 9 is a $^{13}$C NMR spectrum (400 MHz) at 130° C. in tetrachloroethane of the polymer obtained from ethylene homopolymerization using catalyst FI$^2$—Ni$_2$.
Figure 10:
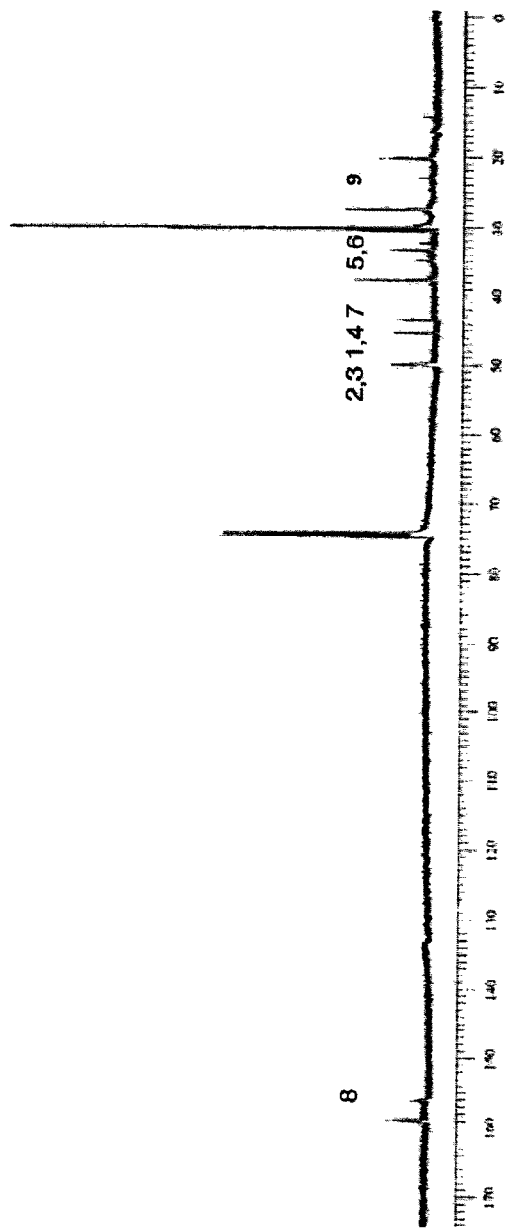
FIG. 10 is a $^{13}$C NMR spectrum (400 MHz) at 130° C. in tetrachloroethane of the polymer obtained from copolymerization of ethylene with NB2 using catalyst FI$^2$—Ni$_2$.
Figure 10:
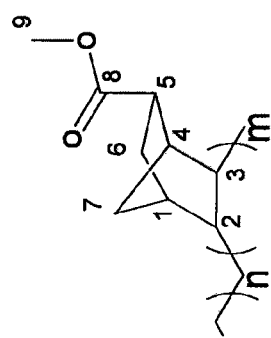
Figure 11:
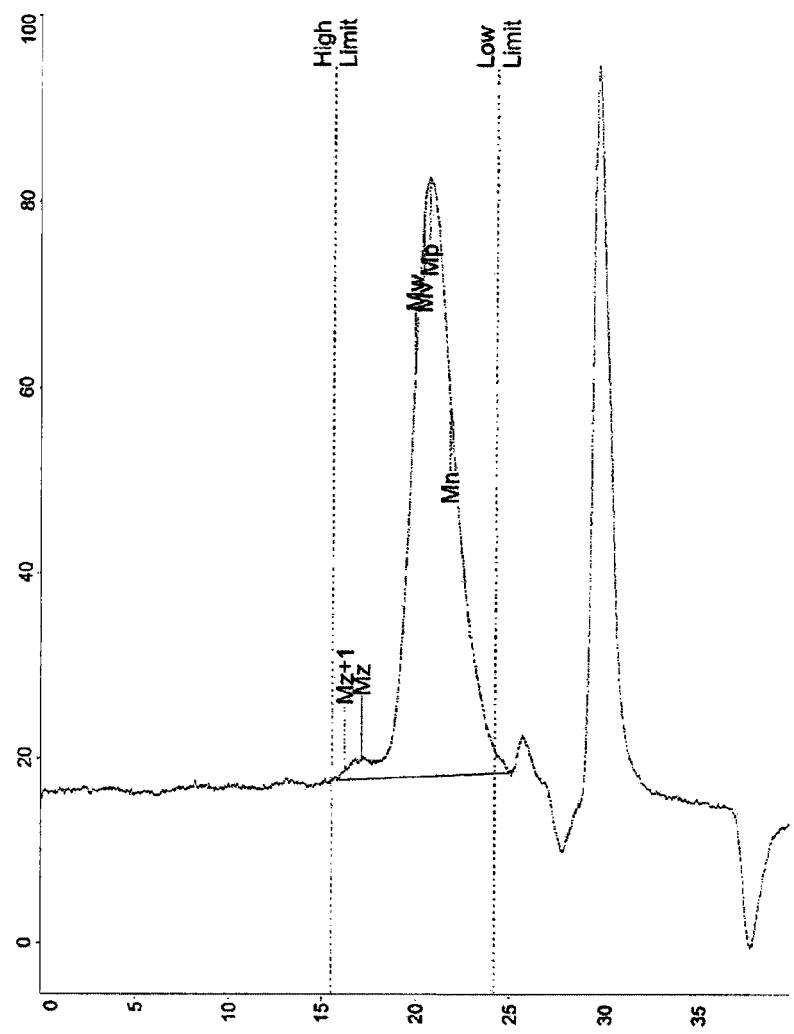
FIG. 11 is a GPC trace for the polymer produced in ethylene/NB2 copolymerizations using catalyst FI$^2$—Ni$_2$.
Figure 12:
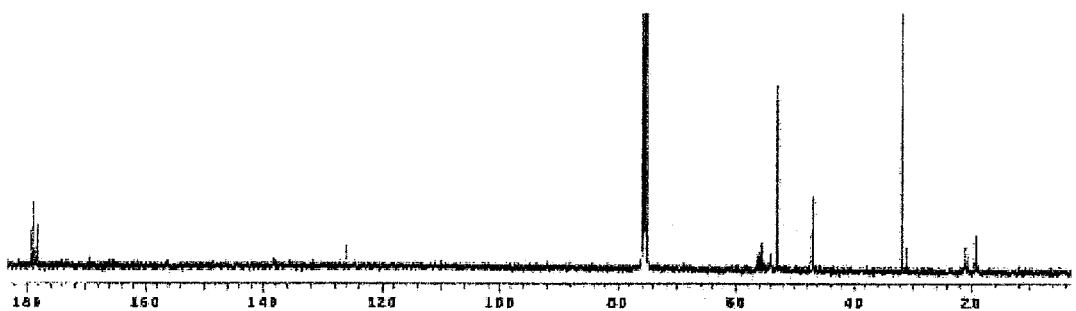
FIG. 12 is a $^{13}$C NMR spectrum (400 MHz) at 130° C. in tetrachloroethane of the polymer obtained from copolymerization of ethylene with MMA using catalyst FI$^2$—Ni$_2$.
Figure 12:
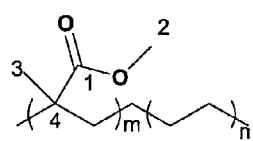
Figure 13:
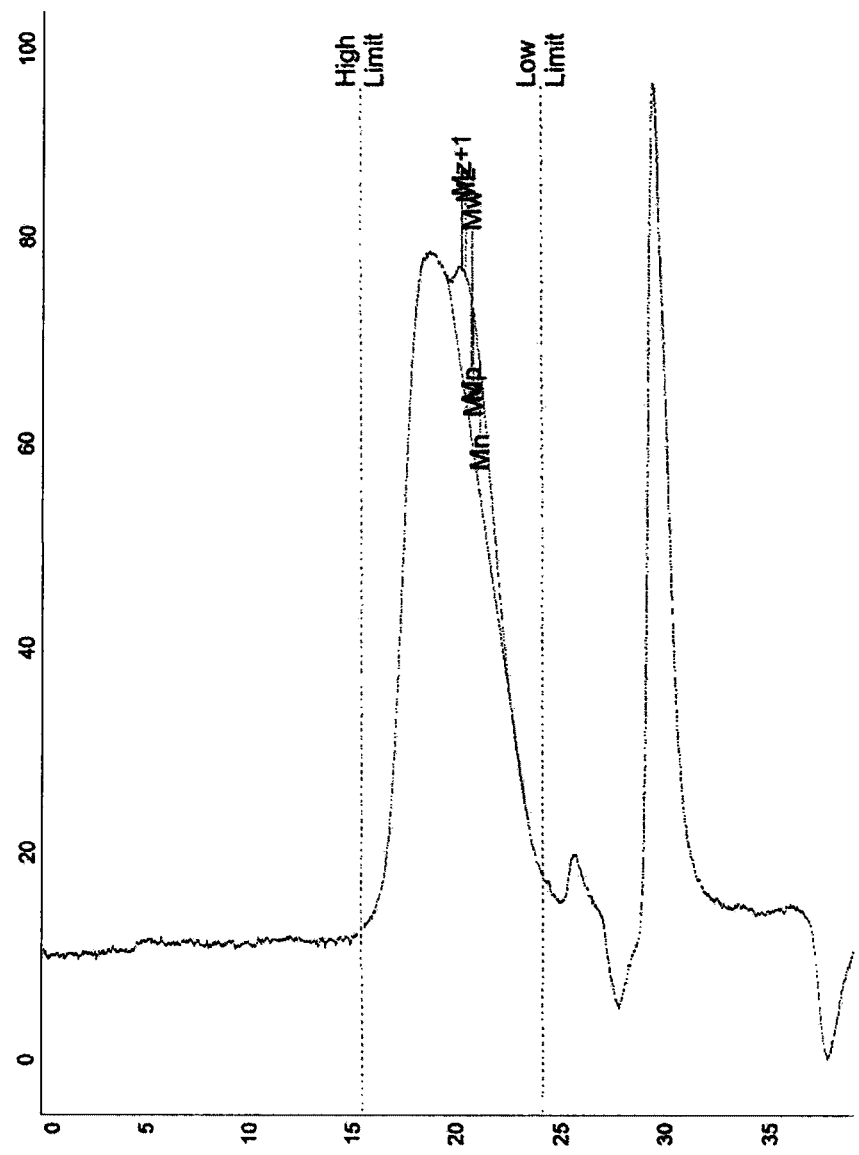
FIG. 13 is a GPC trace for the polymer produced in ethylene/MMA copolymerization using catalyst FI$^2$—Ni$_2$.
Figure 14:
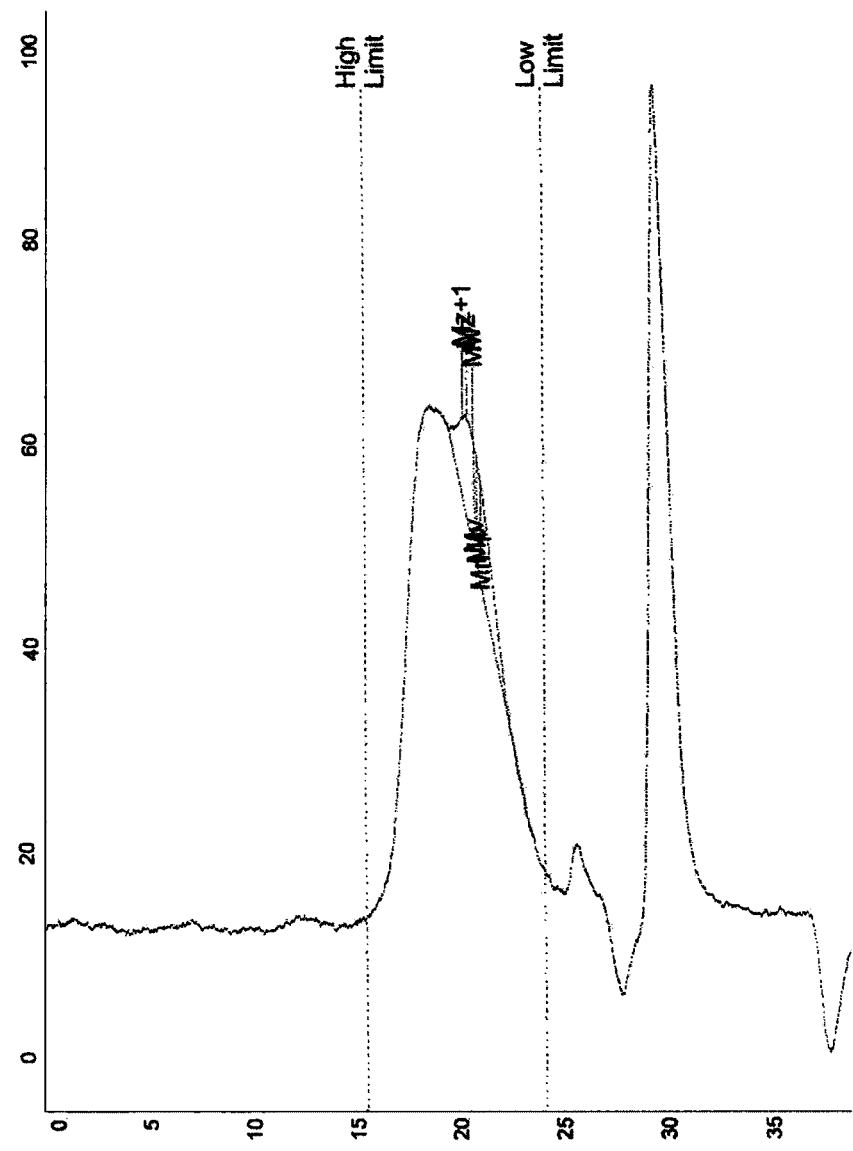
FIG. 14 is a GPC trace for the polymer produced in ethylene/MMA copolymerization using catalyst FI$^2$—Ni$_2$.
Figure 15:
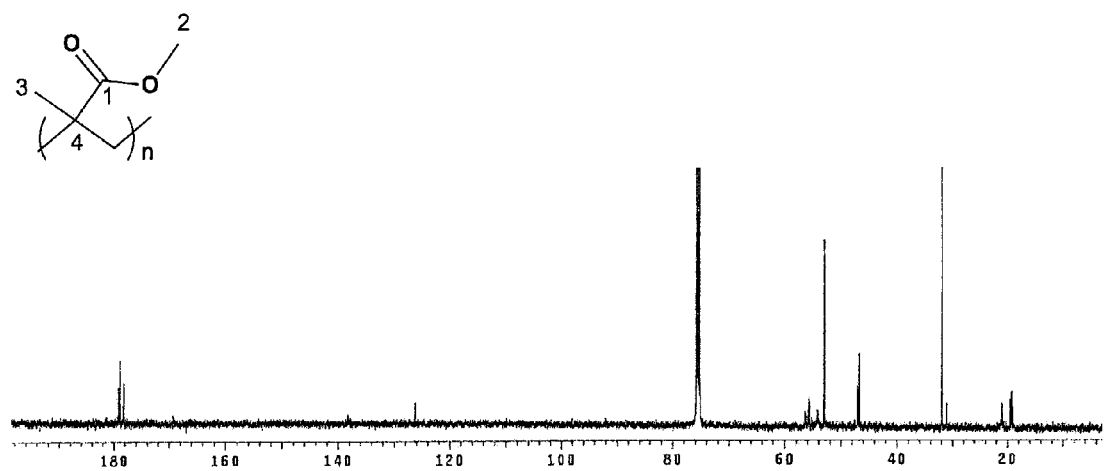
FIG. 15 is a $^{13}$C NMR spectrum (400 MHz) at 130° C. in tetrachloroethane of a commercial PMMA sample (Mw=300,000).
Figure 16:
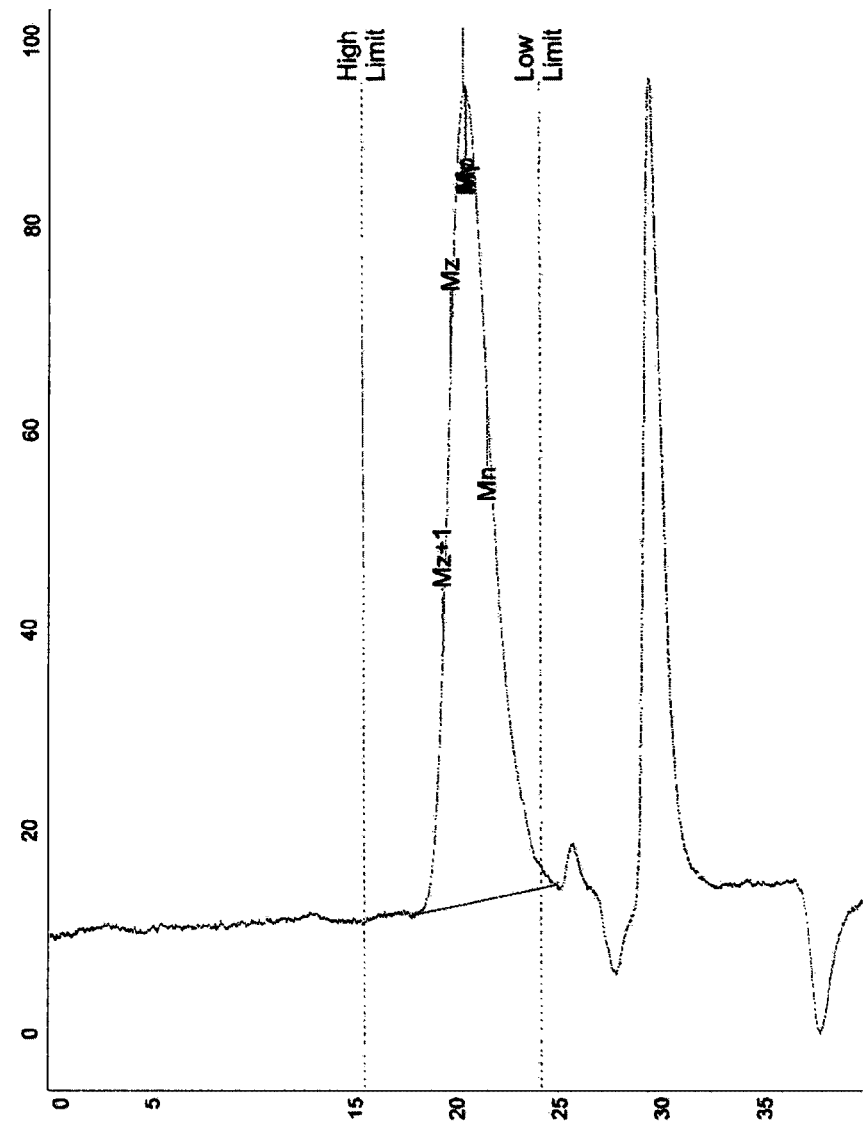
FIG. 16 is a GPC Trace for the polymer produced in ethylene polymerizations with ethyl ether added, using catalyst FI$^2$—Ni$_2$.
Figure 17:
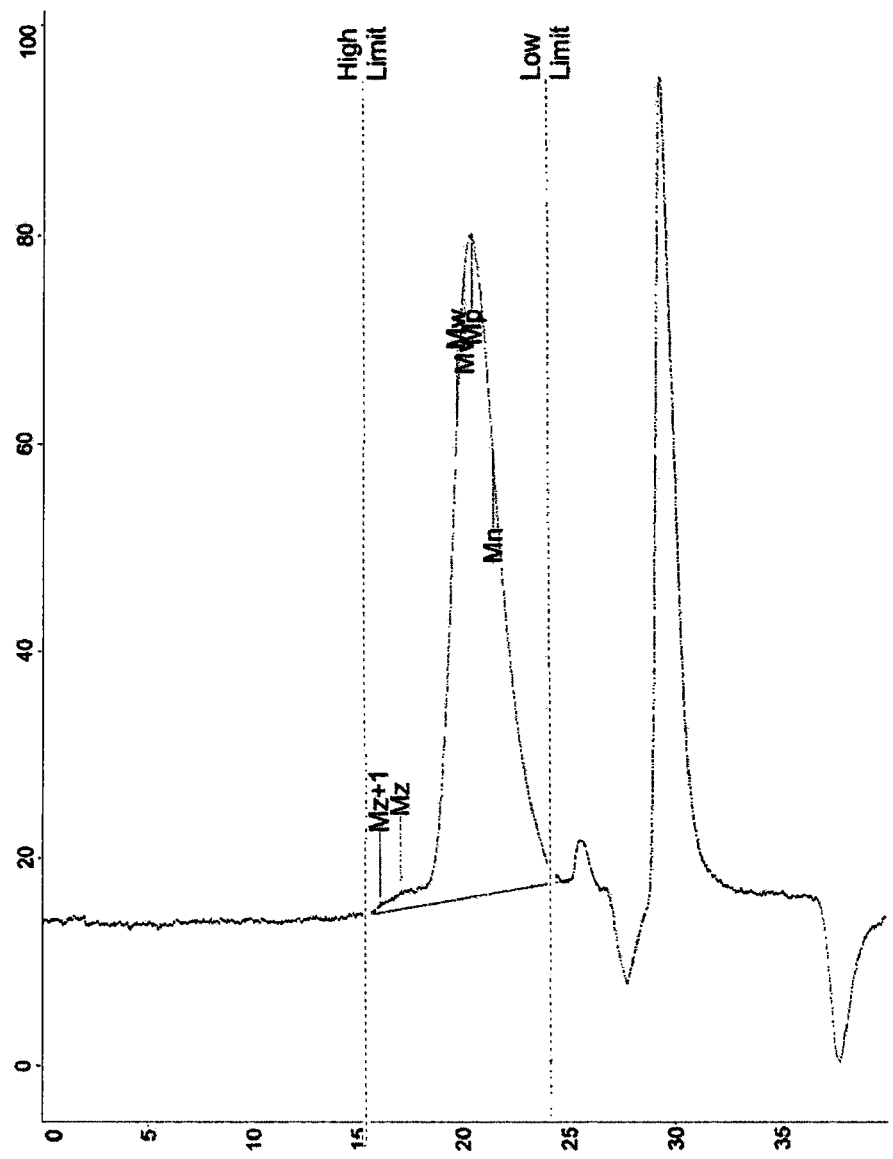
FIG. 17 is a GPC trace for the polymer produced in ethylene polymerizations with acetone added, using catalyst FI$^2$—Ni$_2$.
Figure 18:
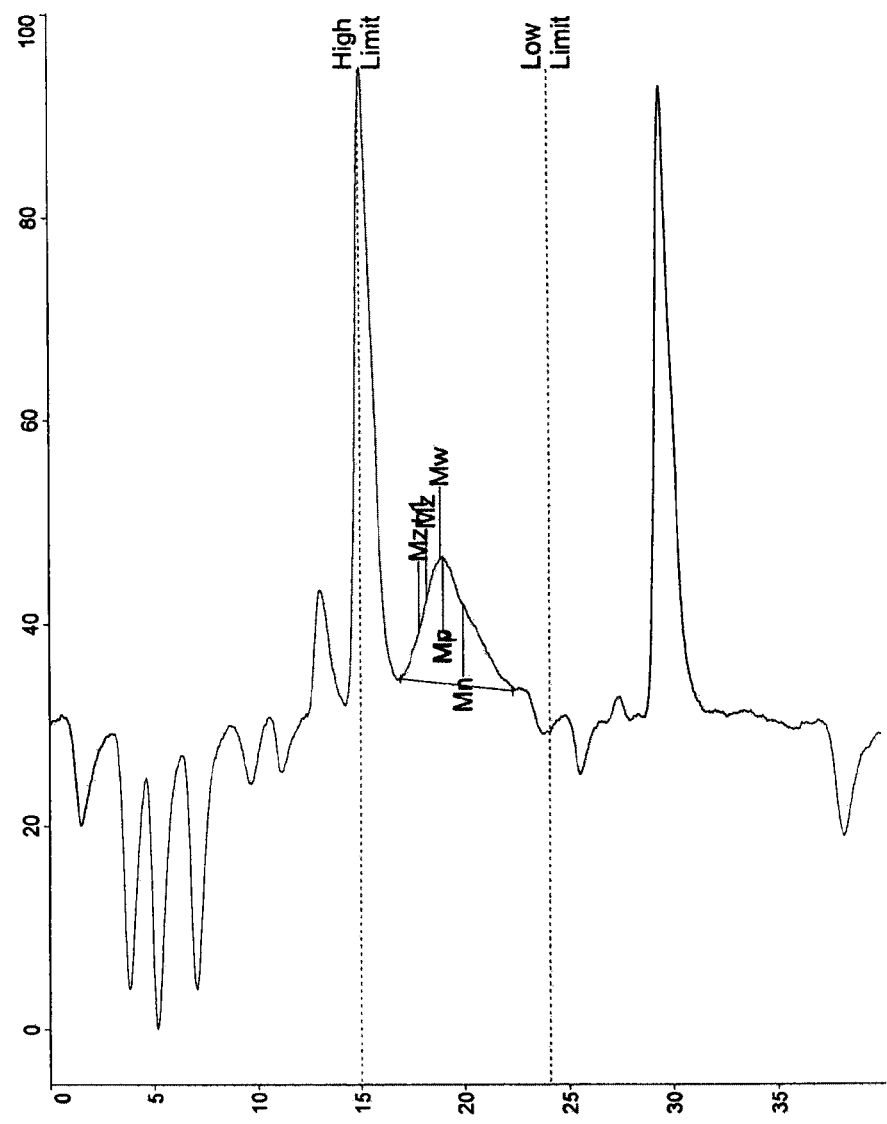
FIG. 18 is a GPC trace of a 1:1 mixture of commercial PMMA ($M_w$~120,000) and PE ($M_w$~70,000).
Figure 19:
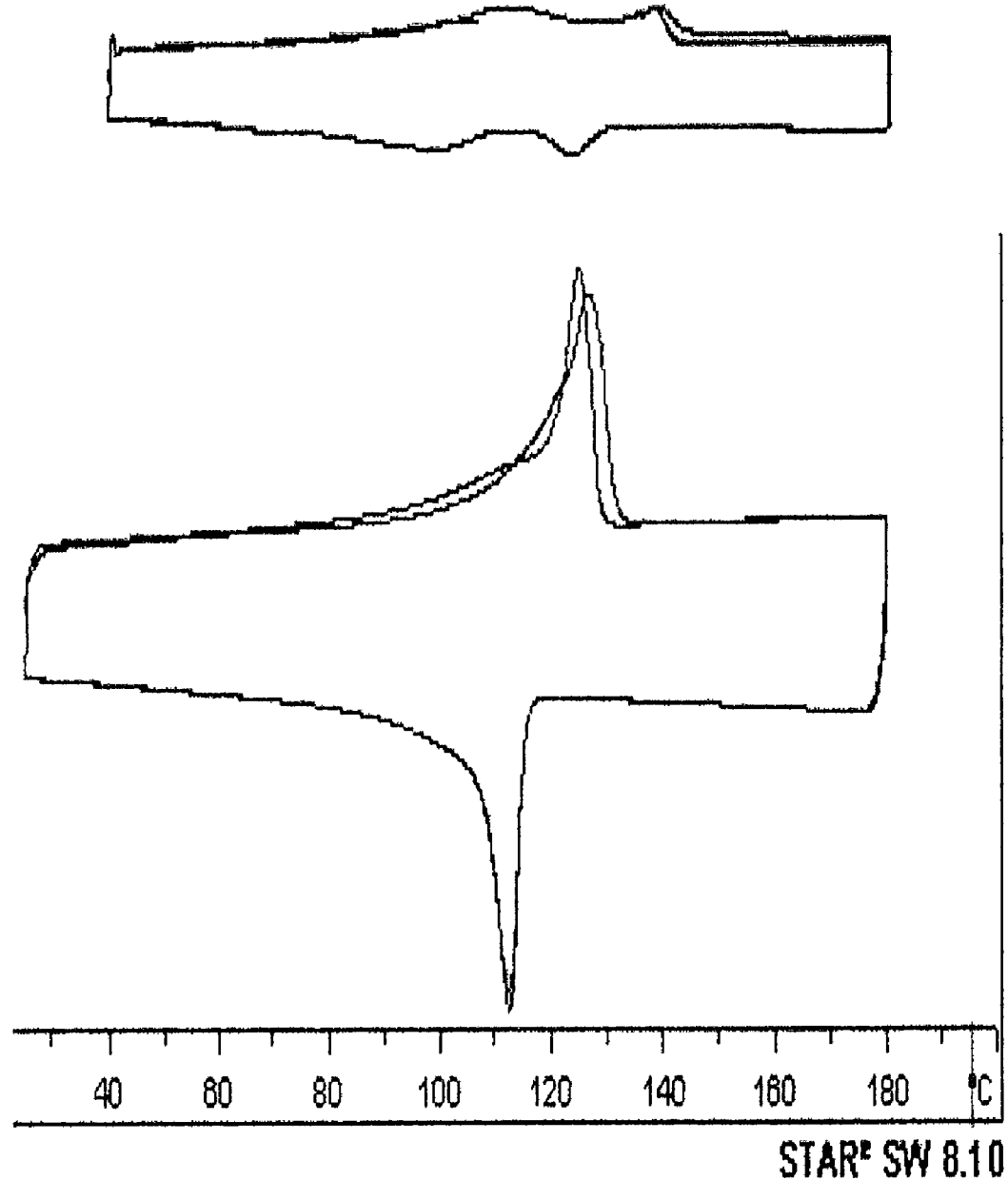
FIG. 19 is a second scan DSC trace of a physical mixture of 1:10 PMMA ($M_w$~120,000): PE ($M_w$~70,000) (top) versus the PE/PMMA copolymer (bottom).
Figure 20:
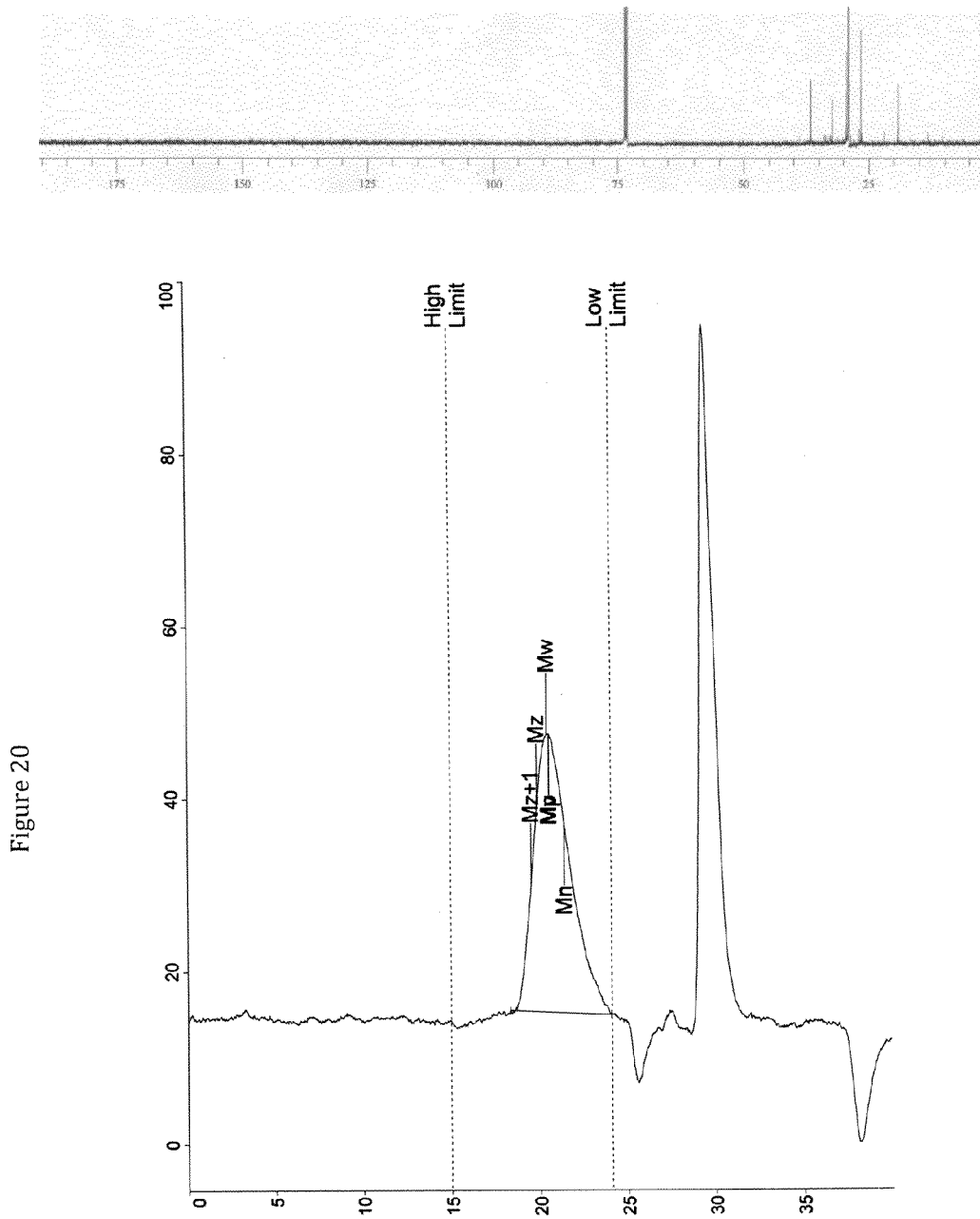
FIG. 20 is $^{13}$C NMR in CDCl$_3$ at room temperature and GPC of the insoluble phase of the 1:1 PMMA ($M_w$~120,000) and PE ($M_w$~70,000) physical mixture after extracting with DCM.
Figure 21:
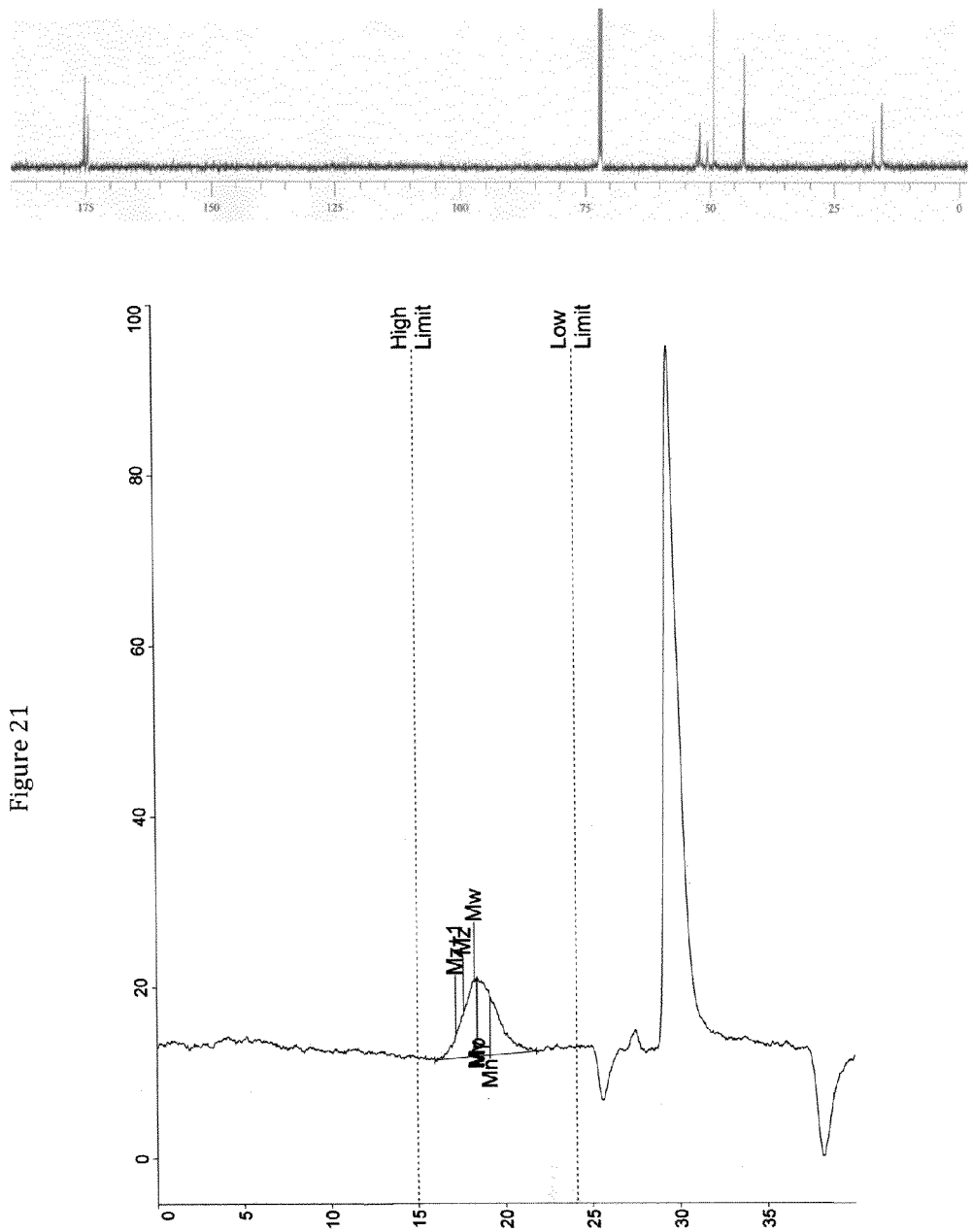
FIG. 21 is $^{13}$C NMR in CDCl$_3$ at room temperature and GPC of the extracted phase of the 1:1 PMMA and PE physical mixture after extracting with DCM.
Figure 22:
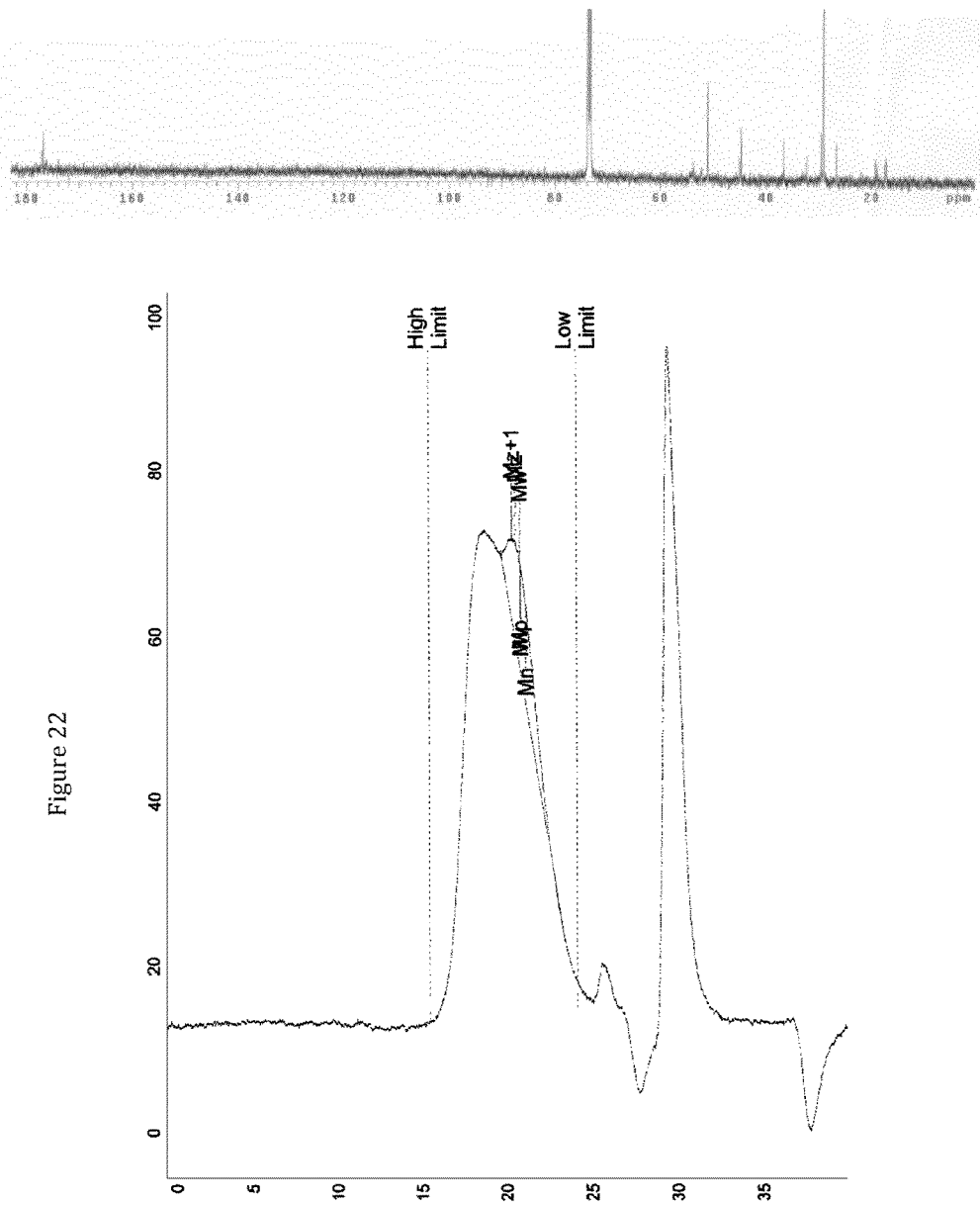
FIG. 22 is a $^{13}$C NMR in CDCl$_3$ at room temperature and GPC of the PE/PMMA copolymer after washing with DCM.

Polymer and Copolymer Characterization Below are shown representative $^{13}C$ NMR spectra and GPC traces for the polymeric products produced in this study. In ethylene homopolymers (FIG. 9), methyl branches, ethyl branches, and carbons α, β, and γ to the branch are assigned at 21.0, 34.2, 39.0, 28.2, and 31.5 ppm, respectively. Signals in similar regions are also observed in the copolymer spectra of FIG. 10 and FIG. 12, but with additional resonances assigned to the corresponding comonomer functional groups. FIG. 15 shows the spectrum of a commercial PMMA sample, which serves as a comparison to the MMA/ethylene copolymer in FIG. 12. Collected samples of both PE and acrylate vary so significantly in physical properties that they can be discerned by the naked eye and separated simply by washing with tetrachloroethane at room temperature. FIGS. 11, 13, 14, 16 and 17 show representative GPC traces of NB/PE and MMA/PE copolymers which are essentially monomodal.

What is claimed is:

1. A catalyst composition comprising a neutral bimetallic diphenoxydiiminate complex of a formula

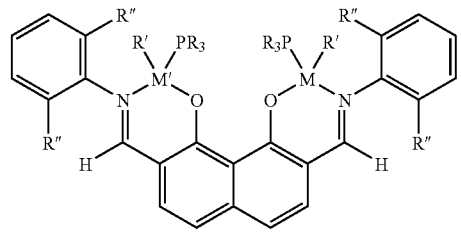

wherein
M and M' are independently selected from Ni, Pd or Pt;
each R is independently selected from alkyl or aryl;
each R' is independently selected from alkyl or aryl; and
each R" is independently selected from alkyl or aryl.

2. The catalyst composition of claim 1 wherein each R" is i-propyl.

3. The catalyst composition of claim 2 wherein M and M' are Ni.

4. The catalyst composition of claim 3 wherein each R' is independently selected from methyl or naphthyl.

5. The catalyst composition of claim 1 wherein the neutral bimetallic diphenoxydiiminate complex is selected from
   a) {2,7-di-[(2,6-diisopropylphenyl)imino]-1,8-naphthalenediolato}bis[(methyl)-(trimethylphosphine)Ni(II)]; or
   b) {2,7-di-[(2,6-diisopropylphenyl)imino]-1,8-naphthalenediolato}bis[(1-naphthyl)-(triphenylphosphine)Ni(II)].

6. A method of preparing an addition polymer comprising
   a) combining a catalyst composition comprising a neutral bimetallic diphenoxydiiminate complex of a formula

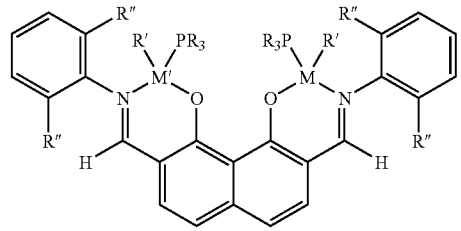

wherein

M and M' are independently selected from Ni, Pd or Pt;

each R is independently selected from alkyl or aryl;

each R' is independently selected from alkyl or aryl; and each R" is independently selected from alkyl or aryl, with one or more olefinic monomeric compounds; and b) polymerizing said one or more olefinic monomeric compounds in the presence of said catalyst composition to form said addition polymer.

7. The method of claim 6 wherein each R" is i-propyl.

8. The method of claim 7 wherein M and M' are Ni.

9. The method of claim 8 wherein each R' is independently selected from methyl or naphthyl.

10. The method of claim 6 wherein the olefinic monomeric compounds are selected from polar olefinic compounds, non-polar olefinic compounds, or combinations of polar and non-polar olefinic compounds.

11. The method of claim 10 wherein the polymerization is selected from homo-polymerization of ethylene or co-polymerization of ethylene with a polar olefinic compound selected from a polar-functionalized norbornene, methyl acrylate or methyl methacrylate.

12. The method of claim 6 wherein the neutral bimetallic diphenoxydiiminate complex is selected from
   a) {2,7-di-[(2,6-diisopropylphenyl)imino]-1,8-naphthalenediolato}bis[(methyl)-(trimethylphosphine)Ni(II)]; or
   b) {2,7-di-[(2,6-diisopropylphenyl)imino]-1,8-naphthalenediolato}bis[(1-naphthyl)-(triphenylphosphine)Ni(II)].

13. The method of claim 12 wherein the catalyst composition further comprises a cocatalyst.

14. The method of claim 13 wherein the cocatalyst is $Ni(cod)_2$.

* * * * *

UNITED STATES PATENT AND TRADEMARK OFFICE
CERTIFICATE OF CORRECTION

| | | |
|---|---|---|
| PATENT NO. | : 8,236,907 B2 | Page 1 of 1 |
| APPLICATION NO. | : 12/574397 | |
| DATED | : August 7, 2012 | |
| INVENTOR(S) | : Tobin J. Marks et al. | |

It is certified that error appears in the above-identified patent and that said Letters Patent is hereby corrected as shown below:

Column 1, Lines 9-13:

"This invention was made with government support under Grant No. CHE 04157407 awarded by the National Science Foundation and Grant No. DE-FG02-86ER13511 awarded by the Department of Energy. The government has certain rights in the invention." should be -- This invention was made with government support under Grant No. CHE4157407 awarded by the National Science Foundation and Grant No. DE-FG02-86ER13511 awarded by the Department of Energy. The government has certain rights in the invention. --

Signed and Sealed this
Twenty-second Day of January, 2013

David J. Kappos
*Director of the United States Patent and Trademark Office*